(12) United States Patent
Agosin Trumper et al.

(10) Patent No.: US 11,124,809 B2
(45) Date of Patent: Sep. 21, 2021

(54) **PRODUCTION OF ALPHA-(R)-(E)-(+)-IONONE IN RECOMBINANT *SACCHAROMYCES CEREVISIAE***

(71) Applicant: Centrome, Inc., Totowa, NJ (US)

(72) Inventors: Eduardo Esteban Agosin Trumper, Santiago (CL); Francisco Javier Saitua Perez, Santiago (CL); Javiera Cecilia Lopez Salinas, Santiago (CL); Maciej E Domaradzki, Glendale, NJ (US); Maximiliano Ibaceta Acevedo, Santiago (CL); Natalia Arenas Frigolett, Santiago (CL)

(73) Assignee: Centrome, Inc., Totowa, NJ (US)

( * ) Notice: Subject to any disclaimer, the term of this patent is extended or adjusted under 35 U.S.C. 154(b) by 0 days.

(21) Appl. No.: 16/230,932

(22) Filed: Dec. 21, 2018

(65) Prior Publication Data

US 2019/0194699 A1 Jun. 27, 2019

Related U.S. Application Data

(60) Provisional application No. 62/609,222, filed on Dec. 21, 2017.

(51) Int. Cl.
*C12P 7/26* (2006.01)
*C12N 9/10* (2006.01)
(Continued)

(52) U.S. Cl.
CPC .............. *C12P 7/26* (2013.01); *C12N 9/0069* (2013.01); *C12N 9/1085* (2013.01); *C12N 9/90* (2013.01);
(Continued)

(58) Field of Classification Search
None
See application file for complete search history.

(56) References Cited

U.S. PATENT DOCUMENTS

2007/0259397 A1* 11/2007 Beekwilder .......... C12N 9/0069
435/68.1
2009/0216039 A1* 8/2009 Yamamoto ............... A23L 2/56
560/128
(Continued)

FOREIGN PATENT DOCUMENTS

WO 2017036495 A1 3/2017

OTHER PUBLICATIONS

UniProt Accession No. A0A0F7SEW9_PHARH, published Jul. 22, 2015 (Year: 2015).*
(Continued)

*Primary Examiner* — Richard C Ekstrom
(74) *Attorney, Agent, or Firm* — Stefan J. Kirchanski; Matthew J. Spark; Zuber Lawler LLP

(57) ABSTRACT

This invention provides improved biological synthesis of the apocarotenoid α-ionone in *Saccharomyces cerevisiae*. The final native step involved in the natural apocarotenoid pathway depends on an endogenous farnesyl pyrophosphate synthase (FPPs). From there, heterologous geranylgeranyl pyrophosphate synthase (crtE), phytoene synthase (crtB), phytoene desaturase (crtI), lycopene ε-cyclase (LycE) and a Carotenoid Cleavage Dioxygenase (CCD1) are required to complete the synthesis of α-ionone. Lycopene ε-cyclase from lettuce (*Lactuca sativa*) or modified cyclase from *Arabidopsis thaliana* was used to overproduce lycopene which was then cleaved by the carotenoid cleavage dioxygenase from *Petunia hybrida* (Ph-CCD1).

9 Claims, 13 Drawing Sheets
Specification includes a Sequence Listing.

(51) Int. Cl.
  *C12N 15/81* (2006.01)
  *C12N 15/52* (2006.01)
  *C12N 9/02* (2006.01)
  *C12N 9/90* (2006.01)

(52) U.S. Cl.
  CPC ............ *C12N 15/52* (2013.01); *C12N 15/81* (2013.01); *C12Y 113/11071* (2015.07); *C12Y 205/01029* (2013.01); *C12Y 505/01018* (2013.01)

(56) References Cited

U.S. PATENT DOCUMENTS

| | | | | |
|---|---|---|---|---|
| 2018/0080031 | A1* | 3/2018 | Wang | C12P 23/00 |
| 2018/0148697 | A1* | 5/2018 | Royer | C12P 19/44 |
| 2018/0251796 | A1* | 9/2018 | Jach | C12P 23/00 |
| 2019/0194699 | A1* | 6/2019 | Agosin Trumper | C12N 9/0069 |
| 2019/0367928 | A1* | 12/2019 | Zhang | C12P 23/00 |

OTHER PUBLICATIONS

Bai, L., Kim, E.H., Dellapenna, D., Brutnell, T.P. (2009) Novel lycopene epsilon cyclase activities in maize revealed through perturbation of carotenoid biosynthesis. Plant J 59:588-599.

Chen, Y., Xiao, W., Wang, Y., Liu, H., Li, X., Yuan, Y. (2016) Lycopene overproduction in *Saccharomyces cerevisiae* through combining pathway engineering with host engineering. Microb Cell Fact 15:113.

Cordero, B.F., Couso, I., Leon, R., Rodriguez, H., Vargas, M.A. (2012) Isolation and characterization of a lycopene ε-Cyclase gene of Chlorella (Chromochloris) zofingiensis. Regulation of the carotenogenic pathway by nitrogen and light. Mar Drugs 10:2069-2088.

Cunningham, F.X., Gantt, E. (2001) One ring or two? Determination of ring number in carotenoids by lycopene ε-cyclases. Proc Natl Acad Sci USA 98:2905-2910.

Gietz, R.D. (2014) Yeast transformation by the LiAc/SS carrier DNA/PG method. In: Yeast Protocols, 3rd edn. Humana Press, New York.

Huang, F.C., Horváth, G., Molnár, P., Turcsi, E., Deli, J., Schrader, J., Sandmann, G., Schmidt, H., Schwab, W. (2009) Substrate promiscuity of RdCCD1, a carotenoid cleavage oxygenase from Rosa damascena. Phytochemistry 70:457-464.

Mikkelsen, M D , Buron, L D , Salomonsen, B., Olsen ,C.E., Hansen, B.G., Mortensen, U.H., Halkier, B.A. (2012) Microbial production of indolylglucosinolate through engineering of a multigene pathway in a versatile yeast expression platform. Metab Eng 14:104-111.

Werkhoff, P., Bretschneider, W., Güntert, M., Hopp, R., Surburg, H. (1991) Chirospecific analysis in flavor and essential oil chemistry part B. Direct enantiomer resolution of trans-α-ionone and trans-α-damascone by inclusion gas chromatography. Eur Food Res Technol 192:111-115.

Wang, C., Liwei, M., Park, J.B., Jeong, S.H., Wei, G., Wang, Y., Kim, S.W. (2018) Microbial Platform for Terpenoid Production: *Escherichia coli* and Yeast. Front. Microbiol. 9:2460.

Xie, W., Lv, X., Ye, L., Zhou, P., Yu, H. (2015) Construction of lycopene-overproducing *Saccharomyces cerevisiae* by combining directed evolution and metabolic engineering. Metab Eng 30:69-78.

Javiera Lopez et al, "Production of [beta]-ionone by combined expression of carotenogenic and plant CCD1 genes in *Saccharomyces cerevisiae*", Microbial Cell Factories, vol. 14, No. 1, Jun. 12, 2015.

Zhang et al, "A 'plug-n-play' modular metabolic system for the production of apocarotenoids", Biotechnology and Bioengineering, vol. 115, No. 1, Nov. 22, 2017, pp. 174-183.

ISA/EPO, International Search Report and Written Opinion from concurrent PCT International Application No. PCT/US2019/067332 dated Mar. 15, 2019.

* cited by examiner

MDYANILTAIPLEFTPQDDIVLLEPYHYLGKNPGKEIRSQLIEAFNYWLDVKKEDLEVIQNVVGML
HTASLLMDDVEDSSVLRRGSPVAHLIYGIPQTINTANYVYFLAYQEIFKLRPTPIPMPVIPPSSASL
QSSVSSASSSSSASSENGGTSTPNSQIPFSKDTYLDKVITDEMLSLHRGQGLELFWRDSLTCPS
EEEYVKMVLGKTGGLFRIAVRLMMAKSECDIDFVQLVNLISIYFQIRDDYMNLQSSEYAHNKNFA
EDLTEGKFSFPTIHSIHANPSSRLVINTLQKKSTSPEILHHCVNYMRTETHSFEYTQEVLNTLSGA
LERELGRLQGEFAEANSRMDLGDVDSEGRTGKNVKLEAILKKLADIPL*

Fig. 3

MSQPPLLDHATQTMANGSKSFATAAKLFDPATRRSVLMLYTWCRHCDDVIDDQTHGFASEAAA
EEEATQRLARLRTLTLAAFEGAEMQDPAFAAFQEVALTHGITPRMALDHLDGFAMDVAQTRYV
TFEDTLRYCYHVAGVVGLMMARVMGVRDERVLDRACDLGLAFQLTNIARDIIDDAAIDRCYLPA
EWLQDAGLTPENYAARENRAALARVAERLIDAAEPYYISSQAGLHDLPPRCAWAIATARSVYRE
IGIKVKAAGGSAWDRRQHTSKGEKIAMLMAAPGQVIRAKTTRVTPRPAGLWQRPV*

Fig. 4

MGLSGATISAPLGCCVLRCGAVGGGKALKADAERWRRAGWSRRVGGPKVRCVATEKHDETAAV
GAAVGVDFADEEDYRKGGGGELLYVQMQSTKPMESQSKIASKLSPISDENTVLDLVIIGCGPAGLS
LASESAKKGLTVGLIGPDLPFTNNYGVWEDEFKDLGLESCIEHVWKDTIVYLDNNKPILIGRSYGRV
HRDLLHEELLKRCYEAGVTYLNSKVDKIIESPDGHRVVCCDKGREIICRLAIVASGAASGRLLEYEVG
GPRVCVQTAYGVEVEVENNPYDPSLMVFMDYRDCFKEEFSHTEQENPTFLYAMPMSPTRVFFEE
TCLASKDAMSFDLLKKRLMYRLNAMGIRILKVYEEEWSYIPVGGSLPNTDQKNLAFGAAASMVHPA
TGYSVVRSLSEAPRYASVISDILGNRVPAEYMLGNSQNYSPSMLAWRTLWPQERKRQRSFFLFGL
ALIIQLNNEGIQTFFEAFFRVPRWMWRGFLGSTLSSVDLILFSFYMFAIAPNQLRMNLVRHLLSDPT
GSSMIKTYLTL*

Fig. 5

MGKEQDQDKPTAIIVGCGIGGIATAARLAKEGFQVTVFEKNDYSGGRCSLIERDGYRFDQGPSLLL
LPDLFKQTFEDLGEKMEDWVDLIKCEPNYVCHFHDEETFTFSTDMALLKREVERFEGKDGFDRFL
SFIQEAHRHYELAVVHVLQKNFPGFAAFLRLQFIGQILALHPFESIWTRVCRYFKTDRLRRVFSFAV
MYMGQSPYSAPGTYSLLQYTELTEGIWYPRGGFWQVPNTLLQIVKRNNPSAKFNFNAPVSQVLLS
PAKDRATGVRLESGEEHHADVVIVNADLVYASEHLIPDDARNKIGQLGEVKRSWWADLVGGKKLK
GSCSSLSFYWSMDRIVDGLGGHNIFLAEDFKGSFDTIFEELGLPADPSFYVNVPSRIDPSAAPEGK
DAIVILVPCGHIDASNPQDYNKLVARARKFVIQTLSAKLGLPDFEKMIVAEKVHDAPSWEKEFNLKD
GSILGLAHNFMQVLGFRPSTRHPKYDKLFFVGASTHPGTGVPIVLAGAKLTANQVLESFDRSPAPD
PNMSLSVPYGKPLKSNGTGIDSQVQLKFMDLERWVYLLVLLIGAVIARSVGVLAF*

Fig. 6

MGLSGATISAPLGCCVLRCGAVGGGKALKADAERWRRAGWSRRVGGPKVRCVATEKHDETAAV
GAAVGVDFADEEDYRKGGGGELLYVQMQSTKPMESQSKIASKLSPISDENTVLDLVIIGCGPAGLS
LASESAKKGLTVGLIGPDLPFTNNYGVWEDEFKDLGLESCIEHVWKDTIVYLDNNKPILIGRSYGRV
HRDLLHEELLKRCYEAGVTYLNSKVDKIIESPDGHRVVCCDKGREIICRLAIVASGAASGRLLEYEVG
GPRVCVQTAYGVEVEVENNPYDPSLMVFMDYRDCFKEEFSHTEQENPTFLYAMPMSPTRVFFEE
TCLASKDAMSFDLLKKRLMYRLNAMGIRILKVYEEEWSYIPVGGSLPNTDQKNLAFGAAASMVHPA
TGYSVVRSLSEAPRYASVISDILGNRVPAEYMLGNSQNYSPSMLAWRTLWPQERKRQRSFFLFGL
ALIIQLNNEGIQTFFEAFFRVPRWMWRGFLGSTLSSVDLILFSFYMFAIAPNQLRMNLVRHLLSDPT
GSSMIKTYLTL*

Fig. 7

MGLSGATISAPLGCCVLRCGAVGGGKALKADAERWRRAGWSRRVGGPKVRCVATEKHDETAAV
GAAVGVDFADEEDYRKGGGGELLYVQMQSTKPMESQSKIASKLSPISDENTVLDLVIIGCGPAGLS
LASESAKKGLTVGLIGPDLPFTNNYGVWEDEFKDLGLESCIEHVWKDTIVYLDNNKPILIGRSYGRV
HRDLLHEELLKRCYEAGVTYLNSKVDKIIESPDGHRVVCCDKGREIICRLAIVASGAASGRLLEYEVG
GPRVCVQTAYGVEVEVENNPYDPSLMVFMDYRDCFKEEFSHTEQENPTFLYAMPMSPTRVFFEE
TCLASKDAMSFDLLKKRLMYRLNAMGIRILKVYEEEWSYIPVGGSLPNTDQKNLAFGAAASMVHPA
TGYSVVRSLSEAPRYASVISDILGNRVPAEYMLGNSQNYSPSMLAWRTLWPQERKRQRSFFLFGL
AHIIQLNNEGIQTFFEAFFRVPRWMWRGFLGSTLSSVDLILFSFYMFAIAPNQLRMNLVRHLLSDPT
GSSMIKTYLTL*

Fig. 8

MECFGARNMTATMAVFTCPRFTDCNIRHKFSLLKQRRFTNLSASSSLRQIKCSAKSDRCVVDKQGI
SVADEEDYVKAGGSELFFVQMQRTKSMESQSKLSEKLAQIPIGNCILDLVVIGCGPAGLALAAESAK
LGLNVGLIGPDLPFTNNYGVWQDEFIGLGLEGCIEHSWKDTLVYLDDADPIRIGRAYGRVHRDLLHE
ELLRRCVESGVSYLSSKVERITEAPNGYSLIECEGNITIPCRLATVASGAASGKFLEYELGGPRVCV
QTAYGIEVEVENNPYDPDLMVFMDYRDFSKHKPESLEAKYPTFLYVMAMSPTKIFFEETCLASREA
MPFNLLKSKLMSRLKAMGIRITRTYEEEWSYIPVGGSLPNTEQKNLAFGAAASMVHPATGYSVVRS
LSEAPNYAAVIAKILRQDQSKEMISLGKYTNISKQAWETLWPLERKRQRAFFLFGLSHIVLMDLEGT
RTFFRTFFRLPKWMWWGFLGSSLSSTDLIIFALYMFVIAPHSLRMELVRHLLSDPTGATMVKAYLTI*

Fig. 9

MGTPAATVVLAFGWHVEFASAYYSHLSWLICWHVLGPTARPIAYEPQTSHYNHSQSCLR
RLLAVASLRLAWVVPTWCCISRANSMQPALVDRPAARCSCLGRQYHTKPFTSHPRTQP
ARQARSNVSVAYPIDAVTTPSPGGGHDHNQAVREGHYEADLVKAQANKQDGEQPKIASI
LQPLQVGTKADAVVVGCGPAGLYLAAQMAQRGLKVGLIGPDVPFVNNYGVWVDEFKQL
GLEHTLECQWPDAVCYFGEGNQVNVGRAYGRVCRRRLRQHLVDLCKSAGVQYLATEV
TDICKSADNTTAYVTCSNGSTFTSRLVTLASGQAAGRFLQYEPEAPAVAAQTAYGIEAEV
EGYDAAYGNDHMLFMDYRRHHTGLWDGGATKLNAGNHPNANDGLWGSSDEVPSFLY
AMPLGGNRVFLEETCLVAKPALPFKVLQRRLERRMRSMGIKVTRIHETEWSYIPVGGPLP
SANQPITAFGAAANLVHPATGFSVSRSLREAPVMAEAAVQALSGSQTVPEVAAAVWQAL
WPDEKRRQASFHLFGMELLAQLDLSATNAFFNTFFALPPTYWKGFLGSRLSSVQLLGFA
LLTFVLAPANIKGKLVSHLMTDPAGRYLISHYISGWSSKESAMTGAPTEAAVAAALMMWQ
LAAATQVQQ*

Fig. 10

MVELSINMSSSLSLESVCSARCFSPSSSAIGAVPGVRRKLCVSVREKPEQPVGAVFVGC
STKHRKSRNHEMWSSSRDCITSAHSAGLDFASSKEGNACATTSSKSGARFLHDEGMGTI
DRAEAVRAQLFPRLNKLSPVKSLRRRCVSPSTRVVTSVLVPPREQYADETDYMKAGGEF
IDLVQLQARKPLQQTKIGEKLEPLSDKLLDLVVIGCGPAGLSLAAEAAKQGLEVGLIGPDLP
FTNNYGVWEDEFAALGLENCIEQIWRDSAMYFESDTPLLIGRAYGRVDRHLLHEELLKRC
ADGGVQYLDTEVERISDADDTGSTVMCANGAVIRCRLVTVASGAAAGRFLEYEPGGPGT
TVQTAYGMEVECENFNYDPEIMLFMDYRDYQAWGTEPCPDADEFKQVPSFLYAMPVSK
TRVFFEETCLAARPTMSFNLLKERLLMRLNSMGIKVVHMYEEEWSYIPVGATLPDTTQQH
LGFGAAASMVHPATGYSVVRSLSEAPHYAAAIASSLRSGGKSVDVNSMVIQSWKHPRAA
ALEAWNALWPSERKRQRAFFLFGLELILQLDLVGIREFFATFFELPEWLWKGFLAAKLSSL
DLIMFALITFVVAPNSLRYRLVRHLMTDPSGSYLIRTYLGLKGTAELPAAKEMR*

Fig. 11

MGRKESDDGVERIEGGVVVVNPKPKKGITAKAIDLLEKVIIKLMHDSSKPLHYLSGNFAPT
DETPPLNDLPIKGHLPECLNGEFVRVGPNPKFAPVAGYHWFDGDGMIHGLRIKDGKATY
VSRYVRTSRLKQEEFFEGAKFMKIGDLKGLFGLFTVYMQMLRAKLKILDTSYGNGTANTA
LVYHHGKLLALSEADKPYALKVLEDGDLQTLGMLDYDKRLLHSFTAHPKVDPVTGEMFTF
GYAHEPPYITYRVISKDGIMQDPVPITIPEAIMMHDFAITENYAIMMDLPLCFRPKEMVKNN
QLAFTFDTTKKARFGVLPRYAKSEALIRWFELPNCFIFHNANAWEEGDEVVLITCRLPHPD
LDMVNGEVKENLENFSNELYEMRFNMKSGAASQKKLSESSVDFPRINENYTGRKQRYV
YGTTLNSIAKVTGIIKFDLHAEPETGKKQLEVGGNVQGIFDLGPGRFGSEAVFVPSQPGTE
CEEDDGYLIFFVHDENTGKSAVNVIDAKTMSAEPVAVVELPKRVPYGFHAFFVTEEQIQE
QAKL*

Fig. 12

SEQUENCE LISTING

```
<160> NUMBER OF SEQ ID NOS: 10

<210> SEQ ID NO 1
<211> LENGTH: 376
<212> TYPE: PRT
<213> ORGANISM: Xanthophyllomyces dendrorhous

<400> SEQUENCE: 1

Met Asp Tyr Ala Asn Ile Leu Thr Ala Ile Pro Leu Glu Phe Thr Pro
1               5                   10                  15

Gln Asp Asp Ile Val Leu Leu Glu Pro Tyr His Tyr Leu Gly Lys Asn
            20                  25                  30

Pro Gly Lys Glu Ile Arg Ser Gln Leu Ile Glu Ala Phe Asn Tyr Trp
        35                  40                  45

Leu Asp Val Lys Lys Glu Asp Leu Glu Val Ile Gln Asn Val Val Gly
    50                  55                  60

Met Leu His Thr Ala Ser Leu Leu Met Asp Asp Val Glu Asp Ser Ser
65                  70                  75                  80

Val Leu Arg Arg Gly Ser Pro Val Ala His Leu Ile Tyr Gly Ile Pro
                85                  90                  95

Gln Thr Ile Asn Thr Ala Asn Tyr Val Tyr Phe Leu Ala Tyr Gln Glu
            100                 105                 110

Ile Phe Lys Leu Arg Pro Thr Pro Ile Pro Met Pro Val Ile Pro Pro
        115                 120                 125

Ser Ser Ala Ser Leu Gln Ser Ser Val Ser Ser Ala Ser Ser Ser Ser
    130                 135                 140

Ser Ala Ser Ser Glu Asn Gly Gly Thr Ser Thr Pro Asn Ser Gln Ile
145                 150                 155                 160

Pro Phe Ser Lys Asp Thr Tyr Leu Asp Lys Val Ile Thr Asp Glu Met
                165                 170                 175
```

-continued

```
Leu Ser Leu His Arg Gly Gln Gly Leu Glu Leu Phe Trp Arg Asp Ser
            180                 185                 190

Leu Thr Cys Pro Ser Glu Glu Tyr Val Lys Met Val Leu Gly Lys
        195                 200                 205

Thr Gly Gly Leu Phe Arg Ile Ala Val Arg Leu Met Met Ala Lys Ser
    210                 215                 220

Glu Cys Asp Ile Asp Phe Val Gln Leu Val Asn Leu Ile Ser Ile Tyr
225                 230                 235                 240

Phe Gln Ile Arg Asp Asp Tyr Met Asn Leu Gln Ser Ser Glu Tyr Ala
                245                 250                 255

His Asn Lys Asn Phe Ala Glu Asp Leu Thr Glu Gly Lys Phe Ser Phe
            260                 265                 270

Pro Thr Ile His Ser Ile His Ala Asn Pro Ser Ser Arg Leu Val Ile
        275                 280                 285

Asn Thr Leu Gln Lys Lys Ser Thr Ser Pro Glu Ile Leu His His Cys
    290                 295                 300

Val Asn Tyr Met Arg Thr Glu Thr His Ser Phe Glu Tyr Thr Gln Glu
305                 310                 315                 320

Val Leu Asn Thr Leu Ser Gly Ala Leu Glu Arg Glu Leu Gly Arg Leu
                325                 330                 335

Gln Gly Glu Phe Ala Glu Ala Asn Ser Arg Met Asp Leu Gly Asp Val
            340                 345                 350

Asp Ser Glu Gly Arg Thr Gly Lys Asn Val Lys Leu Glu Ala Ile Leu
        355                 360                 365

Lys Lys Leu Ala Asp Ile Pro Leu
    370                 375

<210> SEQ ID NO 2
<211> LENGTH: 309
<212> TYPE: PRT
<213> ORGANISM: Pantoea agglomerans

<400> SEQUENCE: 2

Met Ser Gln Pro Pro Leu Leu Asp His Ala Thr Gln Thr Met Ala Asn
1               5                   10                  15

Gly Ser Lys Ser Phe Ala Thr Ala Ala Lys Leu Phe Asp Pro Ala Thr
            20                  25                  30

Arg Arg Ser Val Leu Met Leu Tyr Thr Trp Cys Arg His Cys Asp Asp
        35                  40                  45

Val Ile Asp Asp Gln Thr His Gly Phe Ala Ser Glu Ala Ala Ala Glu
    50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
            100                 105                 110

Leu Asp Gly Phe Ala Met Asp Val Ala Gln Thr Arg Tyr Val Thr Phe
        115                 120                 125

Glu Asp Thr Leu Arg Tyr Cys Tyr His Val Ala Gly Val Val Gly Leu
    130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Ile Ala Arg Asp
                165                 170                 175
```

```
Ile Ile Asp Asp Ala Ala Ile Asp Arg Cys Tyr Leu Pro Ala Glu Trp
            180                 185                 190

Leu Gln Asp Ala Gly Leu Thr Pro Glu Asn Tyr Ala Ala Arg Glu Asn
        195                 200                 205

Arg Ala Ala Leu Ala Arg Val Ala Glu Arg Leu Ile Asp Ala Ala Glu
210                 215                 220

Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
            260                 265                 270

Thr Ser Lys Gly Glu Lys Ile Ala Met Leu Met Ala Ala Pro Gly Gln
        275                 280                 285

Val Ile Arg Ala Lys Thr Thr Arg Val Thr Pro Arg Pro Ala Gly Leu
            290                 295                 300

Trp Gln Arg Pro Val
305

<210> SEQ ID NO 3
<211> LENGTH: 537
<212> TYPE: PRT
<213> ORGANISM: Xanthophyllomyces dendrorhous

<400> SEQUENCE: 3

Met Gly Leu Ser Gly Ala Thr Ile Ser Ala Pro Leu Gly Cys Cys Val
1               5                   10                  15

Leu Arg Cys Gly Ala Val Gly Gly Lys Ala Leu Lys Ala Asp Ala
            20                  25                  30

Glu Arg Trp Arg Arg Ala Gly Trp Ser Arg Arg Val Gly Gly Pro Lys
        35                  40                  45

Val Arg Cys Val Ala Thr Glu Lys His Asp Glu Thr Ala Ala Val Gly
    50                  55                  60

Ala Ala Val Gly Val Asp Phe Ala Asp Glu Glu Asp Tyr Arg Lys Gly
65                  70                  75                  80

Gly Gly Gly Glu Leu Leu Tyr Val Gln Met Gln Ser Thr Lys Pro Met
                85                  90                  95

Glu Ser Gln Ser Lys Ile Ala Ser Lys Leu Ser Pro Ile Ser Asp Glu
            100                 105                 110

Asn Thr Val Leu Asp Leu Val Ile Ile Gly Cys Gly Pro Ala Gly Leu
        115                 120                 125

Ser Leu Ala Ser Glu Ser Ala Lys Lys Gly Leu Thr Val Gly Leu Ile
    130                 135                 140

Gly Pro Asp Leu Pro Phe Thr Asn Asn Tyr Gly Val Trp Glu Asp Glu
145                 150                 155                 160

Phe Lys Asp Leu Gly Leu Glu Ser Cys Ile Glu His Val Trp Lys Asp
                165                 170                 175

Thr Ile Val Tyr Leu Asp Asn Asn Lys Pro Ile Leu Ile Gly Arg Ser
            180                 185                 190

Tyr Gly Arg Val His Arg Asp Leu Leu His Glu Leu Leu Lys Arg
        195                 200                 205

Cys Tyr Glu Ala Gly Val Thr Tyr Leu Asn Ser Lys Val Asp Lys Ile
    210                 215                 220

Ile Glu Ser Pro Asp Gly His Arg Val Val Cys Cys Asp Lys Gly Arg
```

```
                225                 230                 235                 240
Glu Ile Ile Cys Arg Leu Ala Ile Val Ala Ser Gly Ala Ala Ser Gly
                    245                 250                 255

Arg Leu Leu Glu Tyr Glu Val Gly Gly Pro Arg Val Cys Val Gln Thr
                260                 265                 270

Ala Tyr Gly Val Glu Val Glu Glu Asn Asn Pro Tyr Asp Pro Ser
            275                 280                 285

Leu Met Val Phe Met Asp Tyr Arg Asp Cys Phe Lys Glu Glu Phe Ser
        290                 295                 300

His Thr Glu Gln Glu Asn Pro Thr Phe Leu Tyr Ala Met Pro Met Ser
305                 310                 315                 320

Pro Thr Arg Val Phe Phe Glu Glu Thr Cys Leu Ala Ser Lys Asp Ala
                325                 330                 335

Met Ser Phe Asp Leu Leu Lys Lys Arg Leu Met Tyr Arg Leu Asn Ala
                340                 345                 350

Met Gly Ile Arg Ile Leu Lys Val Tyr Glu Glu Glu Trp Ser Tyr Ile
                355                 360                 365

Pro Val Gly Gly Ser Leu Pro Asn Thr Asp Gln Lys Asn Leu Ala Phe
        370                 375                 380

Gly Ala Ala Ala Ser Met Val His Pro Ala Thr Gly Tyr Ser Val Val
385                 390                 395                 400

Arg Ser Leu Ser Glu Ala Pro Arg Tyr Ala Ser Val Ile Ser Asp Ile
                405                 410                 415

Leu Gly Asn Arg Val Pro Ala Glu Tyr Met Leu Gly Asn Ser Gln Asn
                420                 425                 430

Tyr Ser Pro Ser Met Leu Ala Trp Arg Thr Leu Trp Pro Gln Glu Arg
            435                 440                 445

Lys Arg Gln Arg Ser Phe Phe Leu Phe Gly Leu Ala Leu Ile Ile Gln
        450                 455                 460

Leu Asn Asn Glu Gly Ile Gln Thr Phe Glu Ala Phe Phe Arg Val
465                 470                 475                 480

Pro Arg Trp Met Trp Arg Gly Phe Leu Gly Ser Thr Leu Ser Ser Val
                485                 490                 495

Asp Leu Ile Leu Phe Ser Phe Tyr Met Phe Ala Ile Ala Pro Asn Gln
            500                 505                 510

Leu Arg Met Asn Leu Val Arg His Leu Leu Ser Asp Pro Thr Gly Ser
        515                 520                 525

Ser Met Ile Lys Thr Tyr Leu Thr Leu
530                 535

<210> SEQ ID NO 4
<211> LENGTH: 582
<212> TYPE: PRT
<213> ORGANISM: Xanthophyllomyces dendrorhous

<400> SEQUENCE: 4

Met Gly Lys Glu Gln Asp Gln Asp Lys Pro Thr Ala Ile Ile Val Gly
1               5                   10                  15

Cys Gly Ile Gly Gly Ile Ala Thr Ala Ala Arg Leu Ala Lys Glu Gly
                20                  25                  30

Phe Gln Val Thr Val Phe Glu Lys Asn Asp Tyr Ser Gly Gly Arg Cys
            35                  40                  45

Ser Leu Ile Glu Arg Asp Gly Tyr Arg Phe Asp Gln Gly Pro Ser Leu
        50                  55                  60
```

```
Leu Leu Leu Pro Asp Leu Phe Lys Gln Thr Phe Glu Asp Leu Gly Glu
 65                  70                  75                  80

Lys Met Glu Asp Trp Val Asp Leu Ile Lys Cys Glu Pro Asn Tyr Val
                 85                  90                  95

Cys His Phe His Asp Glu Glu Thr Phe Thr Phe Ser Thr Asp Met Ala
            100                 105                 110

Leu Leu Lys Arg Glu Val Glu Arg Phe Glu Gly Lys Asp Gly Phe Asp
        115                 120                 125

Arg Phe Leu Ser Phe Ile Gln Glu Ala His Arg His Tyr Glu Leu Ala
    130                 135                 140

Val Val His Val Leu Gln Lys Asn Phe Pro Gly Phe Ala Ala Phe Leu
145                 150                 155                 160

Arg Leu Gln Phe Ile Gly Gln Ile Leu Ala Leu His Pro Phe Glu Ser
                165                 170                 175

Ile Trp Thr Arg Val Cys Arg Tyr Phe Lys Thr Asp Arg Leu Arg Arg
            180                 185                 190

Val Phe Ser Phe Ala Val Met Tyr Met Gly Gln Ser Pro Tyr Ser Ala
        195                 200                 205

Pro Gly Thr Tyr Ser Leu Leu Gln Tyr Thr Glu Leu Thr Glu Gly Ile
    210                 215                 220

Trp Tyr Pro Arg Gly Gly Phe Trp Gln Val Pro Asn Thr Leu Leu Gln
225                 230                 235                 240

Ile Val Lys Arg Asn Asn Pro Ser Ala Lys Phe Asn Phe Asn Ala Pro
                245                 250                 255

Val Ser Gln Val Leu Leu Ser Pro Ala Lys Asp Arg Ala Thr Gly Val
            260                 265                 270

Arg Leu Glu Ser Gly Glu Glu His His Ala Asp Val Val Ile Val Asn
        275                 280                 285

Ala Asp Leu Val Tyr Ala Ser Glu His Leu Ile Pro Asp Asp Ala Arg
    290                 295                 300

Asn Lys Ile Gly Gln Leu Gly Glu Val Lys Arg Ser Trp Trp Ala Asp
305                 310                 315                 320

Leu Val Gly Gly Lys Lys Leu Lys Gly Ser Cys Ser Ser Leu Ser Phe
                325                 330                 335

Tyr Trp Ser Met Asp Arg Ile Val Asp Gly Leu Gly Gly His Asn Ile
            340                 345                 350

Phe Leu Ala Glu Asp Phe Lys Gly Ser Phe Asp Thr Ile Phe Glu Glu
        355                 360                 365

Leu Gly Leu Pro Ala Asp Pro Ser Phe Tyr Val Asn Val Pro Ser Arg
    370                 375                 380

Ile Asp Pro Ser Ala Ala Pro Glu Gly Lys Asp Ala Ile Val Ile Leu
385                 390                 395                 400

Val Pro Cys Gly His Ile Asp Ala Ser Asn Pro Gln Asp Tyr Asn Lys
                405                 410                 415

Leu Val Ala Arg Ala Arg Lys Phe Val Ile Gln Thr Leu Ser Ala Lys
            420                 425                 430

Leu Gly Leu Pro Asp Phe Glu Lys Met Ile Val Ala Glu Lys Val His
        435                 440                 445

Asp Ala Pro Ser Trp Glu Lys Glu Phe Asn Leu Lys Asp Gly Ser Ile
    450                 455                 460

Leu Gly Leu Ala His Asn Phe Met Gln Val Leu Gly Phe Arg Pro Ser
465                 470                 475                 480

Thr Arg His Pro Lys Tyr Asp Lys Leu Phe Phe Val Gly Ala Ser Thr
```

-continued

```
                485                 490                 495
His Pro Gly Thr Gly Val Pro Ile Val Leu Ala Gly Ala Lys Leu Thr
            500                 505                 510

Ala Asn Gln Val Leu Glu Ser Phe Asp Arg Ser Pro Ala Pro Asp Pro
        515                 520                 525

Asn Met Ser Leu Ser Val Pro Tyr Gly Lys Pro Leu Lys Ser Asn Gly
    530                 535                 540

Thr Gly Ile Asp Ser Gln Val Gln Leu Lys Phe Met Asp Leu Glu Arg
545                 550                 555                 560

Trp Val Tyr Leu Leu Val Leu Leu Ile Gly Ala Val Ile Ala Arg Ser
                565                 570                 575

Val Gly Val Leu Ala Phe
            580

<210> SEQ ID NO 5
<211> LENGTH: 537
<212> TYPE: PRT
<213> ORGANISM: Zea mays

<400> SEQUENCE: 5

Met Gly Leu Ser Gly Ala Thr Ile Ser Ala Pro Leu Gly Cys Cys Val
1               5                   10                  15

Leu Arg Cys Gly Ala Val Gly Gly Lys Ala Leu Lys Ala Asp Ala
            20                  25                  30

Glu Arg Trp Arg Arg Ala Gly Trp Ser Arg Arg Val Gly Gly Pro Lys
        35                  40                  45

Val Arg Cys Val Ala Thr Glu Lys His Asp Glu Thr Ala Ala Val Gly
    50                  55                  60

Ala Ala Val Gly Val Asp Phe Ala Asp Glu Glu Asp Tyr Arg Lys Gly
65                  70                  75                  80

Gly Gly Gly Glu Leu Leu Tyr Val Gln Met Gln Ser Thr Lys Pro Met
                85                  90                  95

Glu Ser Gln Ser Lys Ile Ala Ser Lys Leu Ser Pro Ile Ser Asp Glu
            100                 105                 110

Asn Thr Val Leu Asp Leu Val Ile Ile Gly Cys Gly Pro Ala Gly Leu
        115                 120                 125

Ser Leu Ala Ser Glu Ser Ala Lys Lys Gly Leu Thr Val Gly Leu Ile
    130                 135                 140

Gly Pro Asp Leu Pro Phe Thr Asn Asn Tyr Gly Val Trp Glu Asp Glu
145                 150                 155                 160

Phe Lys Asp Leu Gly Leu Glu Ser Cys Ile Glu His Val Trp Lys Asp
                165                 170                 175

Thr Ile Val Tyr Leu Asp Asn Asn Lys Pro Ile Leu Ile Gly Arg Ser
            180                 185                 190

Tyr Gly Arg Val His Arg Asp Leu Leu His Glu Glu Leu Leu Lys Arg
        195                 200                 205

Cys Tyr Glu Ala Gly Val Thr Tyr Leu Asn Ser Lys Val Asp Lys Ile
    210                 215                 220

Ile Glu Ser Pro Asp Gly His Arg Val Cys Cys Asp Lys Gly Arg
225                 230                 235                 240

Glu Ile Ile Cys Arg Leu Ala Ile Val Ala Ser Gly Ala Ala Ser Gly
                245                 250                 255

Arg Leu Leu Glu Tyr Glu Val Gly Gly Pro Arg Val Cys Val Gln Thr
            260                 265                 270
```

-continued

```
Ala Tyr Gly Val Glu Val Glu Val Glu Asn Asn Pro Tyr Asp Pro Ser
            275                 280                 285

Leu Met Val Phe Met Asp Tyr Arg Asp Cys Phe Lys Glu Glu Phe Ser
290                 295                 300

His Thr Glu Gln Glu Asn Pro Thr Phe Leu Tyr Ala Met Pro Met Ser
305                 310                 315                 320

Pro Thr Arg Val Phe Phe Glu Glu Thr Cys Leu Ala Ser Lys Asp Ala
                325                 330                 335

Met Ser Phe Asp Leu Leu Lys Lys Arg Leu Met Tyr Arg Leu Asn Ala
            340                 345                 350

Met Gly Ile Arg Ile Leu Lys Val Tyr Glu Glu Glu Trp Ser Tyr Ile
        355                 360                 365

Pro Val Gly Gly Ser Leu Pro Asn Thr Asp Gln Lys Asn Leu Ala Phe
    370                 375                 380

Gly Ala Ala Ala Ser Met Val His Pro Ala Thr Gly Tyr Ser Val Val
385                 390                 395                 400

Arg Ser Leu Ser Glu Ala Pro Arg Tyr Ala Ser Val Ile Ser Asp Ile
                405                 410                 415

Leu Gly Asn Arg Val Pro Ala Glu Tyr Met Leu Gly Asn Ser Gln Asn
            420                 425                 430

Tyr Ser Pro Ser Met Leu Ala Trp Arg Thr Leu Trp Pro Gln Glu Arg
        435                 440                 445

Lys Arg Gln Arg Ser Phe Phe Leu Phe Gly Leu Ala Leu Ile Ile Gln
    450                 455                 460

Leu Asn Asn Glu Gly Ile Gln Thr Phe Glu Ala Phe Phe Arg Val
465                 470                 475                 480

Pro Arg Trp Met Trp Arg Gly Phe Leu Gly Ser Thr Leu Ser Ser Val
                485                 490                 495

Asp Leu Ile Leu Phe Ser Phe Tyr Met Phe Ala Ile Ala Pro Asn Gln
            500                 505                 510

Leu Arg Met Asn Leu Val Arg His Leu Leu Ser Asp Pro Thr Gly Ser
        515                 520                 525

Ser Met Ile Lys Thr Tyr Leu Thr Leu
    530                 535

<210> SEQ ID NO 6
<211> LENGTH: 537
<212> TYPE: PRT
<213> ORGANISM: Zea mays

<400> SEQUENCE: 6

Met Gly Leu Ser Gly Ala Thr Ile Ser Ala Pro Leu Gly Cys Cys Val
1               5                   10                  15

Leu Arg Cys Gly Ala Val Gly Gly Lys Ala Leu Lys Ala Asp Ala
            20                  25                  30

Glu Arg Trp Arg Arg Ala Gly Trp Ser Arg Arg Val Gly Gly Pro Lys
        35                  40                  45

Val Arg Cys Val Ala Thr Glu Lys His Asp Glu Thr Ala Ala Val Gly
    50                  55                  60

Ala Ala Val Gly Val Asp Phe Ala Asp Glu Glu Asp Tyr Arg Lys Gly
65                  70                  75                  80

Gly Gly Gly Glu Leu Leu Tyr Val Gln Met Gln Ser Thr Lys Pro Met
                85                  90                  95

Glu Ser Gln Ser Lys Ile Ala Ser Lys Leu Ser Pro Ile Ser Asp Glu
            100                 105                 110
```

-continued

```
Asn Thr Val Leu Asp Leu Val Ile Ile Gly Cys Gly Pro Ala Gly Leu
            115                 120                 125

Ser Leu Ala Ser Glu Ser Ala Lys Lys Gly Leu Thr Val Gly Leu Ile
        130                 135                 140

Gly Pro Asp Leu Pro Phe Thr Asn Asn Tyr Gly Val Trp Glu Asp Glu
145                 150                 155                 160

Phe Lys Asp Leu Gly Leu Glu Ser Cys Ile Glu His Val Trp Lys Asp
                165                 170                 175

Thr Ile Val Tyr Leu Asp Asn Asn Lys Pro Ile Leu Ile Gly Arg Ser
            180                 185                 190

Tyr Gly Arg Val His Arg Asp Leu Leu His Glu Glu Leu Leu Lys Arg
        195                 200                 205

Cys Tyr Glu Ala Gly Val Thr Tyr Leu Asn Ser Lys Val Asp Lys Ile
    210                 215                 220

Ile Glu Ser Pro Asp Gly His Arg Val Val Cys Cys Asp Lys Gly Arg
225                 230                 235                 240

Glu Ile Ile Cys Arg Leu Ala Ile Val Ala Ser Gly Ala Ala Ser Gly
                245                 250                 255

Arg Leu Leu Glu Tyr Glu Val Gly Gly Pro Arg Val Cys Val Gln Thr
            260                 265                 270

Ala Tyr Gly Val Glu Val Glu Val Glu Asn Asn Pro Tyr Asp Pro Ser
        275                 280                 285

Leu Met Val Phe Met Asp Tyr Arg Asp Cys Phe Lys Glu Glu Phe Ser
    290                 295                 300

His Thr Glu Gln Glu Asn Pro Thr Phe Leu Tyr Ala Met Pro Met Ser
305                 310                 315                 320

Pro Thr Arg Val Phe Phe Glu Glu Thr Cys Leu Ala Ser Lys Asp Ala
                325                 330                 335

Met Ser Phe Asp Leu Leu Lys Lys Arg Leu Met Tyr Arg Leu Asn Ala
            340                 345                 350

Met Gly Ile Arg Ile Leu Lys Val Tyr Glu Glu Trp Ser Tyr Ile
        355                 360                 365

Pro Val Gly Gly Ser Leu Pro Asn Thr Asp Gln Lys Asn Leu Ala Phe
    370                 375                 380

Gly Ala Ala Ala Ser Met Val His Pro Ala Thr Gly Tyr Ser Val Val
385                 390                 395                 400

Arg Ser Leu Ser Glu Ala Pro Arg Tyr Ala Ser Val Ile Ser Asp Ile
                405                 410                 415

Leu Gly Asn Arg Val Pro Ala Glu Tyr Met Leu Gly Asn Ser Gln Asn
            420                 425                 430

Tyr Ser Pro Ser Met Leu Ala Trp Arg Thr Leu Trp Pro Gln Glu Arg
        435                 440                 445

Lys Arg Gln Arg Ser Phe Phe Leu Phe Gly Leu Ala His Ile Ile Gln
    450                 455                 460

Leu Asn Asn Glu Gly Ile Gln Thr Phe Phe Glu Ala Phe Phe Arg Val
465                 470                 475                 480

Pro Arg Trp Met Trp Arg Gly Phe Leu Gly Ser Thr Leu Ser Ser Val
                485                 490                 495

Asp Leu Ile Leu Phe Ser Phe Tyr Met Phe Ala Ile Ala Pro Asn Gln
            500                 505                 510

Leu Arg Met Asn Leu Val Arg His Leu Leu Ser Asp Pro Thr Gly Ser
        515                 520                 525
```

```
Ser Met Ile Lys Thr Tyr Leu Thr Leu
    530                 535
```

<210> SEQ ID NO 7
<211> LENGTH: 533
<212> TYPE: PRT
<213> ORGANISM: Lactuca sativa

<400> SEQUENCE: 7

```
Met Glu Cys Phe Gly Ala Arg Asn Met Thr Ala Thr Met Ala Val Phe
1               5                   10                  15

Thr Cys Pro Arg Phe Thr Asp Cys Asn Ile Arg His Lys Phe Ser Leu
            20                  25                  30

Leu Lys Gln Arg Arg Phe Thr Asn Leu Ser Ala Ser Ser Ser Leu Arg
        35                  40                  45

Gln Ile Lys Cys Ser Ala Lys Ser Asp Arg Cys Val Val Asp Lys Gln
    50                  55                  60

Gly Ile Ser Val Ala Asp Glu Asp Tyr Val Lys Ala Gly Gly Ser
65                  70                  75                  80

Glu Leu Phe Phe Val Gln Met Gln Arg Thr Lys Ser Met Glu Ser Gln
                85                  90                  95

Ser Lys Leu Ser Glu Lys Leu Ala Gln Ile Pro Ile Gly Asn Cys Ile
            100                 105                 110

Leu Asp Leu Val Val Ile Gly Cys Gly Pro Ala Gly Leu Ala Leu Ala
        115                 120                 125

Ala Glu Ser Ala Lys Leu Gly Leu Asn Val Gly Leu Ile Gly Pro Asp
    130                 135                 140

Leu Pro Phe Thr Asn Asn Tyr Gly Val Trp Gln Asp Glu Phe Ile Gly
145                 150                 155                 160

Leu Gly Leu Glu Gly Cys Ile Glu His Ser Trp Lys Asp Thr Leu Val
                165                 170                 175

Tyr Leu Asp Asp Ala Asp Pro Ile Arg Ile Gly Arg Ala Tyr Gly Arg
            180                 185                 190

Val His Arg Asp Leu Leu His Glu Glu Leu Leu Arg Arg Cys Val Glu
        195                 200                 205

Ser Gly Val Ser Tyr Leu Ser Ser Lys Val Glu Arg Ile Thr Glu Ala
    210                 215                 220

Pro Asn Gly Tyr Ser Leu Ile Glu Cys Glu Gly Asn Ile Thr Ile Pro
225                 230                 235                 240

Cys Arg Leu Ala Thr Val Ala Ser Gly Ala Ala Ser Gly Lys Phe Leu
                245                 250                 255

Glu Tyr Glu Leu Gly Gly Pro Arg Val Cys Val Gln Thr Ala Tyr Gly
            260                 265                 270

Ile Glu Val Glu Val Glu Asn Asn Pro Tyr Asp Pro Asp Leu Met Val
        275                 280                 285

Phe Met Asp Tyr Arg Asp Phe Ser Lys His Lys Pro Glu Ser Leu Glu
    290                 295                 300

Ala Lys Tyr Pro Thr Phe Leu Tyr Val Met Ala Met Ser Pro Thr Lys
305                 310                 315                 320

Ile Phe Phe Glu Glu Thr Cys Leu Ala Ser Arg Glu Ala Met Pro Phe
                325                 330                 335

Asn Leu Leu Lys Ser Lys Leu Met Ser Arg Leu Lys Ala Met Gly Ile
            340                 345                 350

Arg Ile Thr Arg Thr Tyr Glu Glu Glu Trp Ser Tyr Ile Pro Val Gly
        355                 360                 365
```

Gly Ser Leu Pro Asn Thr Glu Gln Lys Asn Leu Ala Phe Gly Ala Ala
            370                 375                 380

Ala Ser Met Val His Pro Ala Thr Gly Tyr Ser Val Val Arg Ser Leu
385                 390                 395                 400

Ser Glu Ala Pro Asn Tyr Ala Ala Val Ile Ala Lys Ile Leu Arg Gln
                405                 410                 415

Asp Gln Ser Lys Glu Met Ile Ser Leu Gly Lys Tyr Thr Asn Ile Ser
            420                 425                 430

Lys Gln Ala Trp Glu Thr Leu Trp Pro Leu Glu Arg Lys Arg Gln Arg
435                 440                 445

Ala Phe Phe Leu Phe Gly Leu Ser His Ile Val Leu Met Asp Leu Glu
            450                 455                 460

Gly Thr Arg Thr Phe Phe Arg Thr Phe Arg Leu Pro Lys Trp Met
465                 470                 475                 480

Trp Trp Gly Phe Leu Gly Ser Ser Leu Ser Ser Thr Asp Leu Ile Ile
                485                 490                 495

Phe Ala Leu Tyr Met Phe Val Ile Ala Pro His Ser Leu Arg Met Glu
            500                 505                 510

Leu Val Arg His Leu Leu Ser Asp Pro Thr Gly Ala Thr Met Val Lys
            515                 520                 525

Ala Tyr Leu Thr Ile
            530

<210> SEQ ID NO 8
<211> LENGTH: 654
<212> TYPE: PRT
<213> ORGANISM: Chlorella zofingiensis

<400> SEQUENCE: 8

Met Gly Thr Pro Ala Ala Thr Val Val Leu Ala Phe Gly Trp His Val
1               5                   10                  15

Glu Phe Ala Ser Ala Tyr Tyr Ser His Leu Ser Trp Leu Ile Cys Trp
                20                  25                  30

His Val Leu Gly Pro Thr Ala Arg Pro Ile Ala Tyr Glu Pro Gln Thr
            35                  40                  45

Ser His Tyr Asn His Ser Gln Ser Cys Leu Arg Arg Leu Leu Ala Val
        50                  55                  60

Ala Ser Leu Arg Leu Ala Trp Val Val Pro Thr Trp Cys Cys Ile Ser
65                  70                  75                  80

Arg Ala Asn Ser Met Gln Pro Ala Leu Val Asp Arg Pro Ala Ala Arg
                85                  90                  95

Cys Ser Cys Leu Gly Arg Gln Tyr His Thr Lys Pro Phe Thr Ser His
            100                 105                 110

Pro Arg Thr Gln Pro Ala Arg Gln Ala Arg Ser Asn Val Ser Val Ala
        115                 120                 125

Tyr Pro Ile Asp Ala Val Thr Thr Pro Ser Pro Gly Gly Gly His Asp
130                 135                 140

His Asn Gln Ala Val Arg Glu Gly His Tyr Glu Ala Asp Leu Val Lys
145                 150                 155                 160

Ala Gln Ala Asn Lys Gln Asp Gly Glu Gln Pro Lys Ile Ala Ser Ile
                165                 170                 175

Leu Gln Pro Leu Gln Val Gly Thr Lys Ala Asp Ala Val Val Val Gly
            180                 185                 190

Cys Gly Pro Ala Gly Leu Tyr Leu Ala Ala Gln Met Ala Gln Arg Gly

```
                195                 200                 205
Leu Lys Val Gly Leu Ile Gly Pro Asp Val Pro Phe Val Asn Asn Tyr
210                 215                 220
Gly Val Trp Val Asp Glu Phe Lys Gln Leu Gly Leu Glu His Thr Leu
225                 230                 235                 240
Glu Cys Gln Trp Pro Asp Ala Val Cys Tyr Phe Gly Glu Gly Asn Gln
                245                 250                 255
Val Asn Val Gly Arg Ala Tyr Gly Arg Val Cys Arg Arg Leu Arg
            260                 265                 270
Gln His Leu Val Asp Leu Cys Lys Ser Ala Gly Val Gln Tyr Leu Ala
                275                 280                 285
Thr Glu Val Thr Asp Ile Cys Lys Ser Ala Asp Asn Thr Thr Ala Tyr
            290                 295                 300
Val Thr Cys Ser Asn Gly Ser Thr Phe Thr Ser Arg Leu Val Thr Leu
305                 310                 315                 320
Ala Ser Gly Gln Ala Ala Gly Arg Phe Leu Gln Tyr Glu Pro Glu Ala
                325                 330                 335
Pro Ala Val Ala Ala Gln Thr Ala Tyr Gly Ile Glu Ala Glu Val Glu
                340                 345                 350
Gly Tyr Asp Ala Ala Tyr Gly Asn Asp His Met Leu Phe Met Asp Tyr
            355                 360                 365
Arg Arg His His Thr Gly Leu Trp Asp Gly Ala Thr Lys Leu Asn
370                 375                 380
Ala Gly Asn His Pro Asn Ala Asn Asp Gly Leu Trp Gly Ser Ser Asp
385                 390                 395                 400
Glu Val Pro Ser Phe Leu Tyr Ala Met Pro Leu Gly Gly Asn Arg Val
                405                 410                 415
Phe Leu Glu Glu Thr Cys Leu Val Ala Lys Pro Ala Leu Pro Phe Lys
                420                 425                 430
Val Leu Gln Arg Arg Leu Glu Arg Arg Met Arg Ser Met Gly Ile Lys
            435                 440                 445
Val Thr Arg Ile His Glu Thr Glu Trp Ser Tyr Ile Pro Val Gly Gly
            450                 455                 460
Pro Leu Pro Ser Ala Asn Gln Pro Ile Thr Ala Phe Gly Ala Ala Ala
465                 470                 475                 480
Asn Leu Val His Pro Ala Thr Gly Phe Ser Val Ser Arg Ser Leu Arg
                485                 490                 495
Glu Ala Pro Val Met Ala Glu Ala Ala Val Gln Ala Leu Ser Gly Ser
                500                 505                 510
Gln Thr Val Pro Glu Val Ala Ala Val Trp Gln Ala Leu Trp Pro
            515                 520                 525
Asp Glu Lys Arg Arg Gln Ala Ser Phe His Leu Phe Gly Met Glu Leu
            530                 535                 540
Leu Ala Gln Leu Asp Leu Ser Ala Thr Asn Ala Phe Asn Thr Phe
545                 550                 555                 560
Phe Ala Leu Pro Pro Thr Tyr Trp Lys Gly Phe Leu Gly Ser Arg Leu
                565                 570                 575
Ser Ser Val Gln Leu Leu Gly Phe Ala Leu Leu Thr Phe Val Leu Ala
            580                 585                 590
Pro Ala Asn Ile Lys Gly Lys Leu Val Ser His Leu Met Thr Asp Pro
            595                 600                 605
Ala Gly Arg Tyr Leu Ile Ser His Tyr Ile Ser Gly Trp Ser Ser Lys
            610                 615                 620
```

-continued

```
Glu Ser Ala Met Thr Gly Ala Pro Thr Glu Ala Val Ala Ala
625                 630                 635                 640

Leu Met Met Trp Gln Leu Ala Ala Ala Thr Gln Val Gln Gln
                645                 650

<210> SEQ ID NO 9
<211> LENGTH: 650
<212> TYPE: PRT
<213> ORGANISM: Marchantia polymorpha

<400> SEQUENCE: 9

Met Val Glu Leu Ser Ile Asn Met Ser Ser Leu Ser Leu Glu Ser
1               5                   10                  15

Val Cys Ser Ala Arg Cys Phe Ser Pro Ser Ser Ala Ile Gly Ala
                20                  25                  30

Val Pro Gly Val Arg Arg Lys Leu Cys Val Ser Val Arg Glu Lys Pro
                35                  40                  45

Glu Gln Pro Val Gly Ala Val Phe Val Gly Cys Ser Thr Lys His Arg
        50                  55                  60

Lys Ser Arg Asn His Glu Met Trp Ser Ser Ser Arg Asp Cys Ile Thr
65                  70                  75                  80

Ser Ala His Ser Ala Gly Leu Asp Phe Ala Ser Ser Lys Glu Gly Asn
                85                  90                  95

Ala Cys Ala Thr Thr Ser Ser Lys Ser Gly Ala Arg Phe Leu His Asp
                100                 105                 110

Glu Gly Met Gly Thr Ile Asp Arg Ala Glu Ala Val Arg Ala Gln Leu
                115                 120                 125

Phe Pro Arg Leu Asn Lys Leu Ser Pro Val Lys Ser Leu Arg Arg Arg
        130                 135                 140

Cys Val Ser Pro Ser Thr Arg Val Val Thr Ser Val Leu Val Pro Pro
145                 150                 155                 160

Arg Glu Gln Tyr Ala Asp Glu Thr Asp Tyr Met Lys Ala Gly Gly Glu
                165                 170                 175

Phe Ile Asp Leu Val Gln Leu Gln Ala Arg Lys Pro Leu Gln Gln Thr
                180                 185                 190

Lys Ile Gly Glu Lys Leu Glu Pro Leu Ser Asp Lys Leu Leu Asp Leu
                195                 200                 205

Val Val Ile Gly Cys Gly Pro Ala Gly Leu Ser Leu Ala Ala Glu Ala
        210                 215                 220

Ala Lys Gln Gly Leu Glu Val Gly Leu Ile Gly Pro Asp Leu Pro Phe
225                 230                 235                 240

Thr Asn Asn Tyr Gly Val Trp Glu Asp Glu Phe Ala Ala Leu Gly Leu
                245                 250                 255

Glu Asn Cys Ile Glu Gln Ile Trp Arg Asp Ser Ala Met Tyr Phe Glu
                260                 265                 270

Ser Asp Thr Pro Leu Leu Ile Gly Arg Ala Tyr Gly Arg Val Asp Arg
                275                 280                 285

His Leu Leu His Glu Leu Leu Lys Arg Cys Ala Asp Gly Gly Val
        290                 295                 300

Gln Tyr Leu Asp Thr Glu Val Glu Arg Ile Ser Asp Ala Asp Thr
305                 310                 315                 320

Gly Ser Thr Val Met Cys Ala Asn Gly Ala Val Ile Arg Cys Arg Leu
                325                 330                 335

Val Thr Val Ala Ser Gly Ala Ala Ala Gly Arg Phe Leu Glu Tyr Glu
```

-continued

```
                    340                 345                 350
            Pro Gly Gly Pro Gly Thr Thr Val Gln Thr Ala Tyr Gly Met Glu Val
                        355                 360                 365
            Glu Cys Glu Asn Phe Asn Tyr Asp Pro Glu Ile Met Leu Phe Met Asp
                    370                 375                 380
            Tyr Arg Asp Tyr Gln Ala Trp Gly Thr Glu Pro Cys Pro Asp Ala Asp
            385                 390                 395                 400
            Glu Phe Lys Gln Val Pro Ser Phe Leu Tyr Ala Met Pro Val Ser Lys
                            405                 410                 415
            Thr Arg Val Phe Phe Glu Glu Thr Cys Leu Ala Ala Arg Pro Thr Met
                        420                 425                 430
            Ser Phe Asn Leu Leu Lys Glu Arg Leu Leu Met Arg Leu Asn Ser Met
                    435                 440                 445
            Gly Ile Lys Val Val His Met Tyr Glu Glu Trp Ser Tyr Ile Pro
                450                 455                 460
            Val Gly Ala Thr Leu Pro Asp Thr Thr Gln Gln His Leu Gly Phe Gly
            465                 470                 475                 480
            Ala Ala Ala Ser Met Val His Pro Ala Thr Gly Tyr Ser Val Val Arg
                            485                 490                 495
            Ser Leu Ser Glu Ala Pro His Tyr Ala Ala Ile Ala Ser Ser Leu
                        500                 505                 510
            Arg Ser Gly Gly Lys Ser Val Asp Val Asn Ser Met Val Ile Gln Ser
                    515                 520                 525
            Trp Lys His Pro Arg Ala Ala Ala Leu Glu Ala Trp Asn Ala Leu Trp
                530                 535                 540
            Pro Ser Glu Arg Lys Arg Gln Arg Ala Phe Phe Leu Phe Gly Leu Glu
            545                 550                 555                 560
            Leu Ile Leu Gln Leu Asp Leu Val Gly Ile Arg Glu Phe Phe Ala Thr
                            565                 570                 575
            Phe Phe Glu Leu Pro Glu Trp Leu Trp Lys Gly Phe Leu Ala Ala Lys
                        580                 585                 590
            Leu Ser Ser Leu Asp Leu Ile Met Phe Ala Leu Ile Thr Phe Val Val
                    595                 600                 605
            Ala Pro Asn Ser Leu Arg Tyr Arg Leu Val Arg His Leu Met Thr Asp
                610                 615                 620
            Pro Ser Gly Ser Tyr Leu Ile Arg Thr Tyr Leu Gly Leu Lys Gly Thr
            625                 630                 635                 640
            Ala Glu Leu Pro Ala Ala Lys Glu Met Arg
                            645                 650

<210> SEQ ID NO 10
<211> LENGTH: 546
<212> TYPE: PRT
<213> ORGANISM: Petunia hybrida

<400> SEQUENCE: 10

Met Gly Arg Lys Glu Ser Asp Asp Gly Val Glu Arg Ile Glu Gly Gly
            1               5                   10                  15
            Val Val Val Asn Pro Lys Pro Lys Lys Gly Ile Thr Ala Lys Ala
                        20                  25                  30
            Ile Asp Leu Leu Glu Lys Val Ile Lys Leu Met His Asp Ser Ser
                    35                  40                  45
            Lys Pro Leu His Tyr Leu Ser Gly Asn Phe Ala Pro Thr Asp Glu Thr
                50                  55                  60
```

```
Pro Pro Leu Asn Asp Leu Pro Ile Lys Gly His Leu Pro Glu Cys Leu
 65                  70                  75                  80

Asn Gly Glu Phe Val Arg Val Gly Pro Asn Pro Lys Phe Ala Pro Val
                 85                  90                  95

Ala Gly Tyr His Trp Phe Asp Gly Asp Gly Met Ile His Gly Leu Arg
            100                 105                 110

Ile Lys Asp Gly Lys Ala Thr Tyr Val Ser Arg Tyr Val Arg Thr Ser
        115                 120                 125

Arg Leu Lys Gln Glu Glu Phe Phe Glu Gly Ala Lys Phe Met Lys Ile
    130                 135                 140

Gly Asp Leu Lys Gly Leu Phe Gly Leu Phe Thr Val Tyr Met Gln Met
145                 150                 155                 160

Leu Arg Ala Lys Leu Lys Ile Leu Asp Thr Ser Tyr Gly Asn Gly Thr
                165                 170                 175

Ala Asn Thr Ala Leu Val Tyr His His Gly Lys Leu Leu Ala Leu Ser
            180                 185                 190

Glu Ala Asp Lys Pro Tyr Ala Leu Lys Val Leu Glu Asp Gly Asp Leu
        195                 200                 205

Gln Thr Leu Gly Met Leu Asp Tyr Asp Lys Arg Leu Leu His Ser Phe
    210                 215                 220

Thr Ala His Pro Lys Val Asp Pro Val Thr Gly Glu Met Phe Thr Phe
225                 230                 235                 240

Gly Tyr Ala His Glu Pro Pro Tyr Ile Thr Tyr Arg Val Ile Ser Lys
                245                 250                 255

Asp Gly Ile Met Gln Asp Pro Val Pro Ile Thr Ile Pro Glu Ala Ile
            260                 265                 270

Met Met His Asp Phe Ala Ile Thr Glu Asn Tyr Ala Ile Met Met Asp
        275                 280                 285

Leu Pro Leu Cys Phe Arg Pro Lys Glu Met Val Lys Asn Asn Gln Leu
    290                 295                 300

Ala Phe Thr Phe Asp Thr Thr Lys Lys Ala Arg Phe Gly Val Leu Pro
305                 310                 315                 320

Arg Tyr Ala Lys Ser Glu Ala Leu Ile Arg Trp Phe Glu Leu Pro Asn
                325                 330                 335

Cys Phe Ile Phe His Asn Ala Asn Ala Trp Glu Glu Gly Asp Glu Val
            340                 345                 350

Val Leu Ile Thr Cys Arg Leu Pro His Pro Asp Leu Asp Met Val Asn
        355                 360                 365

Gly Glu Val Lys Glu Asn Leu Glu Asn Phe Ser Asn Glu Leu Tyr Glu
    370                 375                 380

Met Arg Phe Asn Met Lys Ser Gly Ala Ala Ser Gln Lys Lys Leu Ser
385                 390                 395                 400

Glu Ser Ser Val Asp Phe Pro Arg Ile Asn Glu Asn Tyr Thr Gly Arg
                405                 410                 415

Lys Gln Arg Tyr Val Tyr Gly Thr Thr Leu Asn Ser Ile Ala Lys Val
            420                 425                 430

Thr Gly Ile Ile Lys Phe Asp Leu His Ala Glu Pro Glu Thr Gly Lys
        435                 440                 445

Lys Gln Leu Glu Val Gly Gly Asn Val Gln Gly Ile Phe Asp Leu Gly
    450                 455                 460

Pro Gly Arg Phe Gly Ser Glu Ala Val Phe Val Pro Ser Gln Pro Gly
465                 470                 475                 480

Thr Glu Cys Glu Glu Asp Asp Gly Tyr Leu Ile Phe Phe Val His Asp
```

-continued

```
                485                 490                 495
Glu Asn Thr Gly Lys Ser Ala Val Asn Val Ile Asp Ala Lys Thr Met
            500                 505                 510

Ser Ala Glu Pro Val Ala Val Val Glu Leu Pro Lys Arg Val Pro Tyr
            515                 520                 525

Gly Phe His Ala Phe Phe Val Thr Glu Glu Gln Ile Gln Glu Gln Ala
            530                 535                 540

Lys Leu
545
```

PRODUCTION OF ALPHA-(R)-(E)-(+)-IONONE IN RECOMBINANT *SACCHAROMYCES CEREVISIAE*

CROSS-REFERENCE TO PRIOR APPLICATIONS

The present application is based on and claims the priority and benefit of U.S. Provisional Patent Application Ser. No. 62/609,222 filed on 21 Dec. 2017.

GOVERNMENT SUPPORT

Not applicable.

BACKGROUND

Area of the Art

The present invention is in the area of biotechnology and is more specifically directed to synthesis of α-ionone by fermentation using genetically modified strains of *Saccharomyces cerevisiae*.

Description of the Background

Isoprenoids, also called terpenoids, are the largest and most diverse group of compounds found in nature, mostly in plants. Their biochemical role in cells is diverse, ranging from cell membrane components, through functions in subcellular targeting and regulation, to plant defense, communication, and pigmentation. Terpenoids also have attractive commercial applications as flavor and fragrance additives in the food and cosmetic industry.

Given the wide applications of isoprenoids, studies in recent decades have focused on optimization of their production. Extraction from native plant sources is often cumbersome, since these natural compounds accumulate at very low quantities over long growth periods. Their purification requires separation from a multitude of other compounds of similar structure, and yields are subject to regional, seasonal, and environmental factors. Chemical synthesis, on the other hand, has several problems due to the complex reaction sequences and the production of enantiomeric and diasteriomeric mixtures, which requires subsequent separation steps. An alternative process to plant extraction and chemical synthesis is the heterologous expression of terpenoid-producing-enzymes in industrial, microbial hosts.

Furthermore, with the development of genetic engineering tools, it is possible to optimize biosynthesis of heterologous products through microbial fermentation to boost production to levels much higher than those found in plant hosts. Microbial hosts thus provide stable production strains amenable to growth medium improvements. Therefore, the choice of host strain carries advantages and disadvantages specific to the requirements of the production methods that may also be related to the end use. For example, the bacterium *Escherichia coli* is often a preferred host for genetic engineering of isoprenoid pathways, yet it is less favorable for food and health applications. On the other hand, the eukaryotic yeast *Saccharomyces cerevisiae* has a long history of use for beer, wine, and bread production as well as extensive use as a host for bio-based applications and heterologous pathway development. Microbial processes and host platform organisms considered to be a GRAS (Generally Regarded As Safe) are favored in the food and aroma industries. Many fungi satisfy GRAS requirement, and increasingly have genetic tools useful for improving industrial robustness with product yield in the multi-gram range providing an ideal as a cell factory (see reference 9).

Apocarotenoids are a subclass of isoprenoids highly appreciated in the flavoring industry due to their characteristic aromatic notes. In plants, apocarotenoids are produced by the cleavage of carotenoids ($C_{40}$) by the enzymatic action of CODs (carotenoid cleavage dioxygenases), a family of oxidative enzymes that specifically cleave double bonds. The apocarotenoid, (R)-(E)-(+)-alpha-ionone ((R,E)-+-4-(2,6,6-trimethylcyclohex-2-en-1-yl) but-3-en-2-one)), is an almost colorless, oily liquid often described having a sweet, woody taste with a fruity fragrance. This compound is considered one of the main aromas of raspberry along with raspberry ketone, and β-damascenone. Thus, α-ionone is widely used in fragrance products, such as perfumes, body lotions, shampoos, and deodorants, with additional use in the food industry as flavoring agent. Natural occurrence of α-ionone has been identified in various flowers, fruits, and leaves, contributing significantly to their characteristic aromas.

However, these natural sources often contain concentrations of α-ionone in parts per million, making direct extraction and purification prohibitively expensive. Therefore, most of the α-ionone available in these markets is synthesized from petrochemicals. As a chiral molecule, α-ionone has two enantiomeric states (R and S, see FIG. 1). The rectus (R) isomer is the major natural enantiomer (natural extracts have an enantiomeric composition of 95-99.9% of (R)-α-ionone), and its fragrance has been described as more floral and fruity than the corresponding sinister (S) enantiomer (see reference 8). Current industrial methods for the synthesis of α-ionone yield a racemic mixture. Although some enantioselective syntheses have been researched, these methods have not found industrial applicability in the natural flavor and fragrance market. The current invention presents a method for enantiomerically pure (R)-(E)-(+)-alpha-ionone synthesis by fermentation using engineered yeast cells, preferably those of *Saccharomyces cerevisiae*.

PRIOR ART

Phytowelt Green Technologies is a globally active R & D company whose core business is plant biotechnology. It has focused on α-ionone production by *Escherichia coli* bacterial cells. Recently, this company was granted a patent (WO2017036495 A1) on a method for the preparation of enantiomerically pure α-ionone in *E. coli*. In this patent application neither the performance of the strain, nor final yields were described and/or disclosed. The patented invention further relates to a process for preparing high-purity ε-carotene.

Recently, Wang et al. (2018) (reference 9) reported the production of α-ionone in the *E. coli* BI21-Gold DE3 strain. By simultaneously expressing 13 different enzymes in four types of inducible plasmids, the authors reported a final yield of 30 mg/L in flasks cultures. In this study, the lycopene ε-cyclase gene (LsLCYe) from *Lactuca sativa*, crtY gene from *Pantoea ananatis* and the CCD1 gene from *Osmanthus fragrans* were codon-optimized for its expression in bacteria. All these genes were cloned and expressed in episomal plasmids requiring cultivation in the presence of antibiotics as a selective pressure. To increase the concentration of ε-carotene, a series of N-terminal truncated LsLCYe were also constructed. The removal of the first 50 amino acids resulted in 40% increase in enzymatic expression, with a two-fold increase in the ε-carotene production. Finally, the authors described the use of isopropyl myristate to entrap the apocarotenoids during fermentations, producing the highest concentration of α-ionone described for bacterial cells.

SUMMARY OF THE INVENTION

This invention provides improved biological synthesis of α-ionone which belongs to the $C_{13}$-apocarotenoid or $C_{13}$-norisoprenoid class of compounds. Apocarotenoids are natural aromatic compounds produced in green land plants by the enzymatic cleavage of carotenoids. Carotenes are forty-carbon molecules ($C_{40}$) whose biosynthesis depends on the availability of $C_5$ isoprene-building units. Isoprene biosynthesis can be carried out through the mevalonate pathway (MVA) or, alternatively, by the 1-deoxy-D-xylulose-5-phosphate (DXP) pathway. Because MVA pathway is naturally present in *S. cerevisiae*, the present invention uses this organism for carotene biosynthesis. The last native step involved in the natural apocarotenoid pathway depends on an endogenous farnesyl pyrophosphate synthase (FPPs). From there, heterologous geranylgeranyl pyrophosphate synthase (crtE), phytoene synthase (crtB), phytoene desaturase (crtI), lycopene ε-cyclase (LycE) and a Carotenoid Cleavage Dioxygenase (CCD1) are required to complete the synthesis of α-ionone.

Lycopene ε-cyclase from lettuce (*Lactuca sativa*) performs an effective double cyclization of lycopene to produce primarily ε-carotene. Using modified proteins and site-specific mutations (single amino acid mutation of leucine to histidine) gives *A. thaliana* LycE double cyclization activity similar to lycopene ε-cyclases from *L. sativa* in *E. coli* cells. Although both δ- and ε-carotenes could be substrates for CCD1 cleavage for α-ionone production, ε-carotene provides better yields because the stoichiometry produces two molecules of α-ionone per molecule of ε-carotene. Five different lycopene ε-cyclase candidates were screened to find the most effective sequence for the yeast platform.

Geranylgeranyl pyrophosphate synthase from *Xanthophyllomyces dendrorhous* (Xd-crtE); phytoene synthase from *Pantoea agglomerans* (Pa-crtB) or the mutant bifunctional phytoene synthase/lycopene cyclase from *Xanthophyllomyces dendrorhous* (Xd-crtYB*) can be used to produce a tetraterpene ($C_{40}$) overproducing *Saccharomyces cerevisiae* that accumulated up to 1.61 g/L of lycopene in a fed-batch glucose fermentation.

Phytoene desaturase from *Blakeslea trispora* (Bt-crtI) or Phytoene desaturase from *Xanthophyllomyces dendrorhous* were used for host and pathway engineering in *Saccharomyces cerevisiae* to overproduce lycopene. Pathway engineering included enzyme screening of different phytoene desaturases (crtI).

Carotenoid cleavage dioxygenase from *Petunia hybrida* (Ph-CCD1): to obtain final α-ionone strain(s) it is necessary to express a CCD1 gene to cleave δ and/or ε-carotene. CCD1 enzymes cleavage substrates include either β- or ε-ring carotenoids.

To reconstruct the α-ionone pathway in *S. cerevisiae* it is necessary to clone the carotenogenic genes into suitable expression vectors. The most commonly used plasmids in yeast are integrative and episomal vectors. Although an increase in the number of gene copies can be seen by using episomal vectors, gene integration is preferable due to the resulting higher strain stability over time. In order to perform vector integration, some sequence modules are required for the DNA recombination, strain selection, marker recycling and gene expression. The plasmids used allow integration and expression in a divergent mode of two or more genes per each vector due to the presence of a bidirectional fused promoter, or in a tandem mode, separating the genes by different promoters. Two or more different transcription terminator sequences are placed downstream of each gene, thereby preventing unwanted recombination events.

These vectors can be constructed by using different molecular biological techniques: including restriction cloning or PCR-based seamless cloning such as Gibson Assembly or Golden Gate Assembly. Transformation of yeast with integrative vectors can be performed according to general protocols for LiAc/SS carrier DNA/PEG method. Characterization of the generated strains allowed selection of candidates with the best productive potential. Shake flask cultures containing YPD (yeast extract 10 g/L, peptone 20 g/L, dextrose 20 g/L) medium were used and carotenoids and aroma profiles were studied for each new strain. Carotenoids were extracted in hexane from 48-hour flask cultures. The resulting organic phase was directly analyzed by reverse phase HPLC. Carotenoids quantification in strains allows identification of possible bottlenecks in the pathway. For $C_{13}$-apocarotenoid quantification, including α-ionone, supernatants obtained from 72-hour cultures were extracted with 10% (v/v) dodecane and analyzed by GC-MS.

DESCRIPTION OF THE FIGURES

FIG. 3 is the amino acid sequence of geranylgeranyl pyrophosphate synthase from *Xanthophyllomyces dendrorhous* (Xd-crtE) (SEQ ID NO:1);

FIG. 4 is the amino acid sequence of geranylgeranyl pyrophosphate synthase phytoene synthase from *Pantoea agglomerans* (Pa-crtB) (SEQ ID NO:2);

FIG. 5 is the amino acid sequence of lycopene ε-cyclase from *Zea mays* (Zm-LycE) (SEQ ID NO: 3);

FIG. 6 is the amino acid sequence of phytoene desaturase from *Xanthophyllomyces dendrorhous* (Xd-crtI) (SEQ ID NO:4);

FIG. 7 is the amino acid sequence of lycopene ε-cyclase from *Zea mays* (Zm-LycE) (SEQ ID NO:5);

FIG. 8 is the amino acid sequence of L461H mutant lycopene ε-cyclase from *Zea mays* (Zm-LycE) (SEQ ID NO:6);

FIG. 9 is the amino acid sequence of lycopene ε-cyclase from *Lactuca sativa* (Ls-LycE) (SEQ ID NO:7);

FIG. 10 is the amino acid sequence of lycopene ε-cyclase from green alga *Chlorella zofingiensis* (Cz-LycE) (SEQ ID NO:8);

FIG. 11 is the amino acid sequence of lycopene ε-cyclase from the liverwort *Marchantia polymorpha* (Mp-LycE) (SEQ ID NO:9);

FIG. 12 is the amino acid sequence of carotenoid cleavage dioxygenase from *Petunia hybrida* (Ph-CCD1) (SEQ ID NO:10);

DETAILED DESCRIPTION OF THE INVENTION

Figure 1:
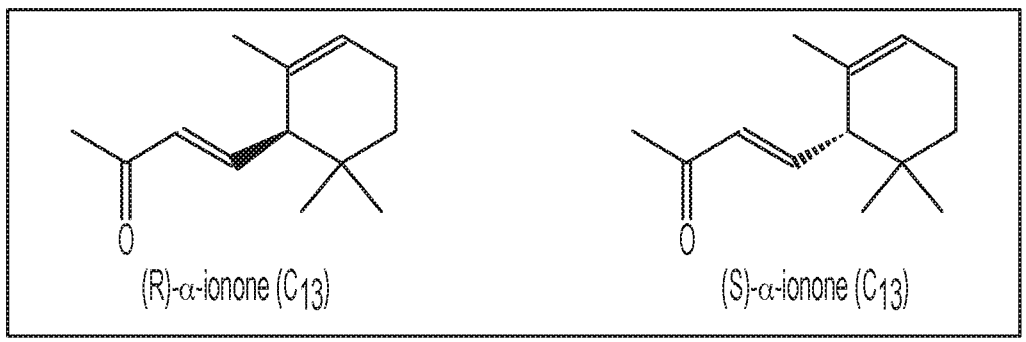
FIG. 1 shows the chemical structures of (R)-(E)-(+)-alpha-ionone and (S)-(E)-(−)-alpha-ionone.
Figure 2:
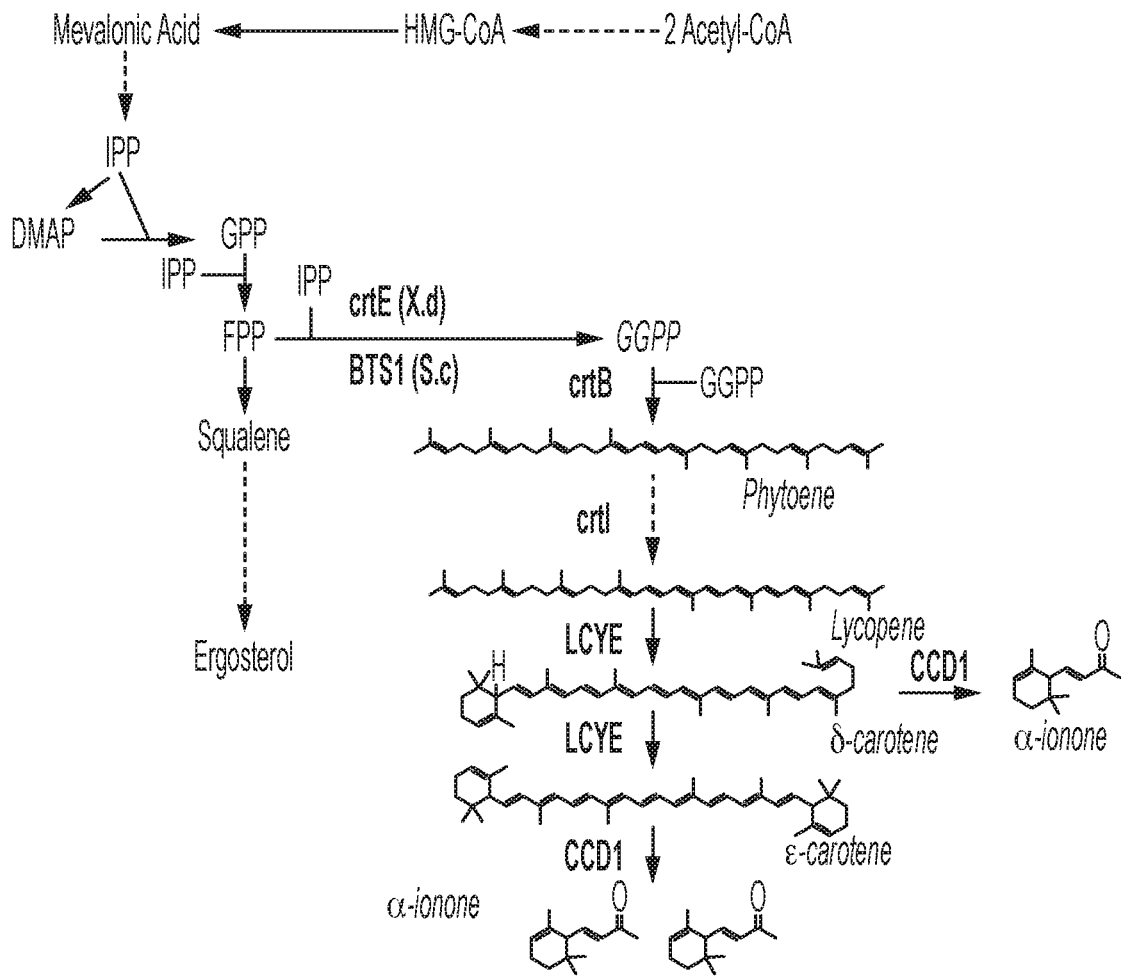
FIG. 2 shows a heterologous pathway for the synthesis of α-ionone.
Figure 13:
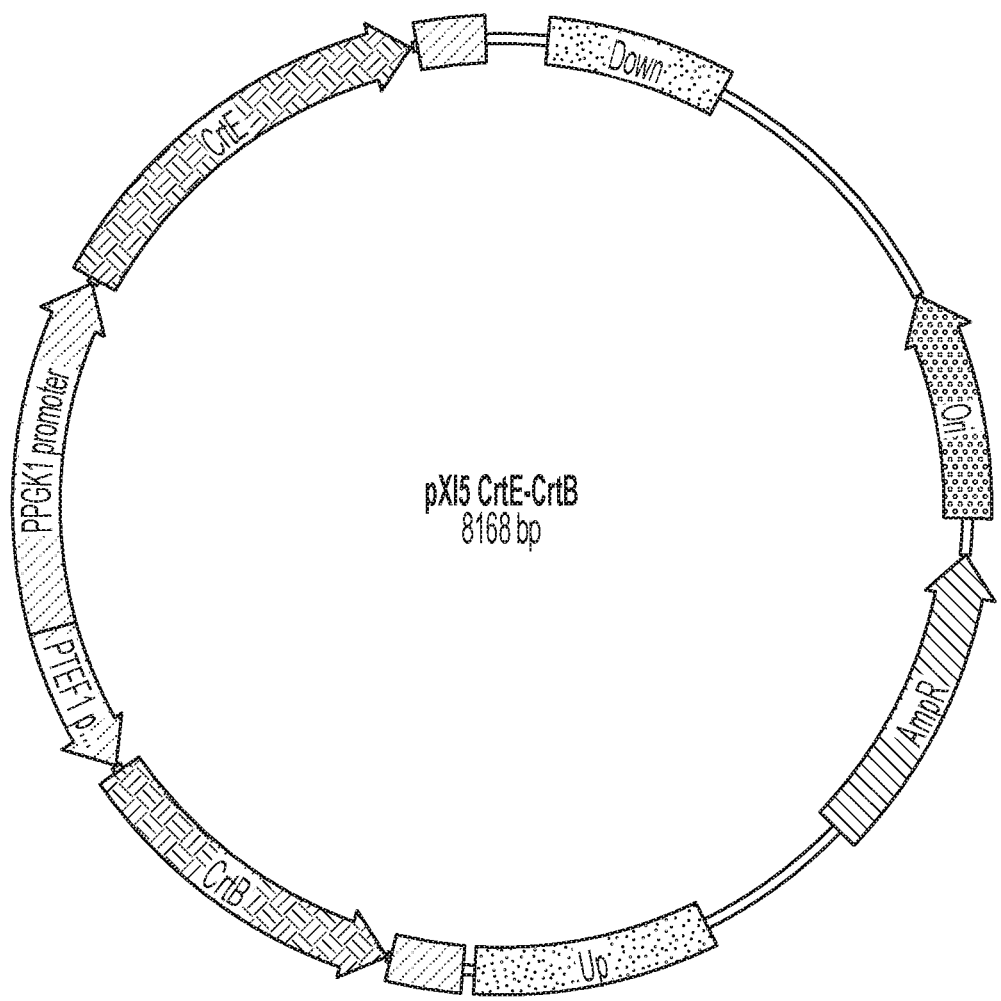
FIG. 13 is a plasmid map of an XI-5 divergent vector containing the crtE and crtB genes.
Figure 14:
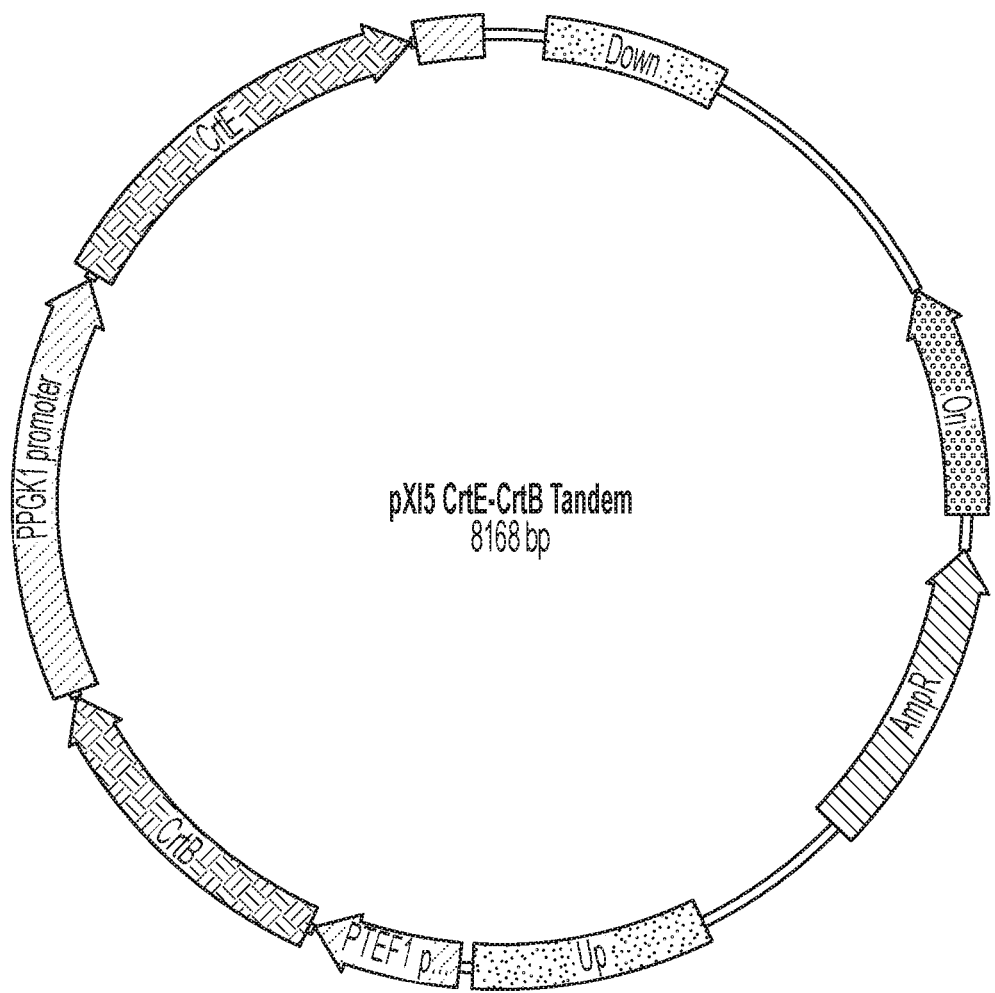
FIG. 14 is a plasmid map of an XI-5 tandem vector containing the crtE and crtB genes.
Figure 15:
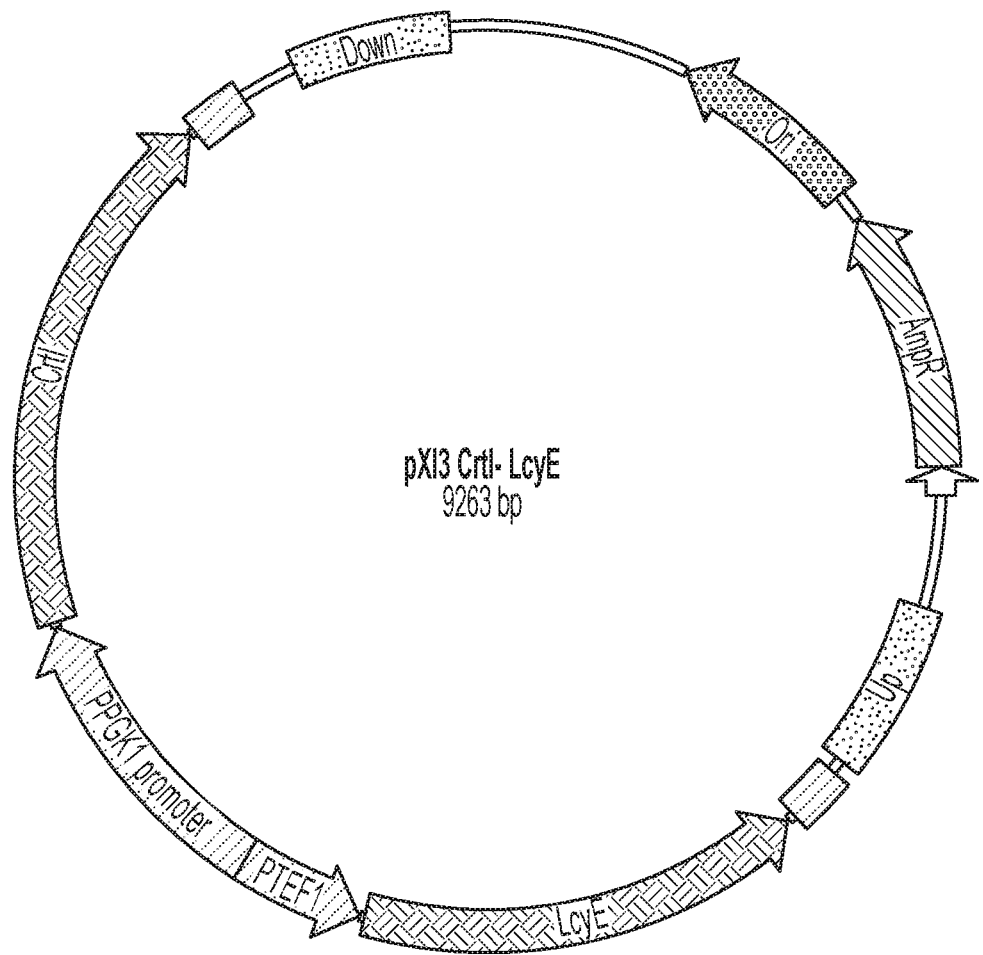
FIG. 15 is a plasmid map of an XI-3 divergent vector containing the crtI and lycE genes.
Figure 16:
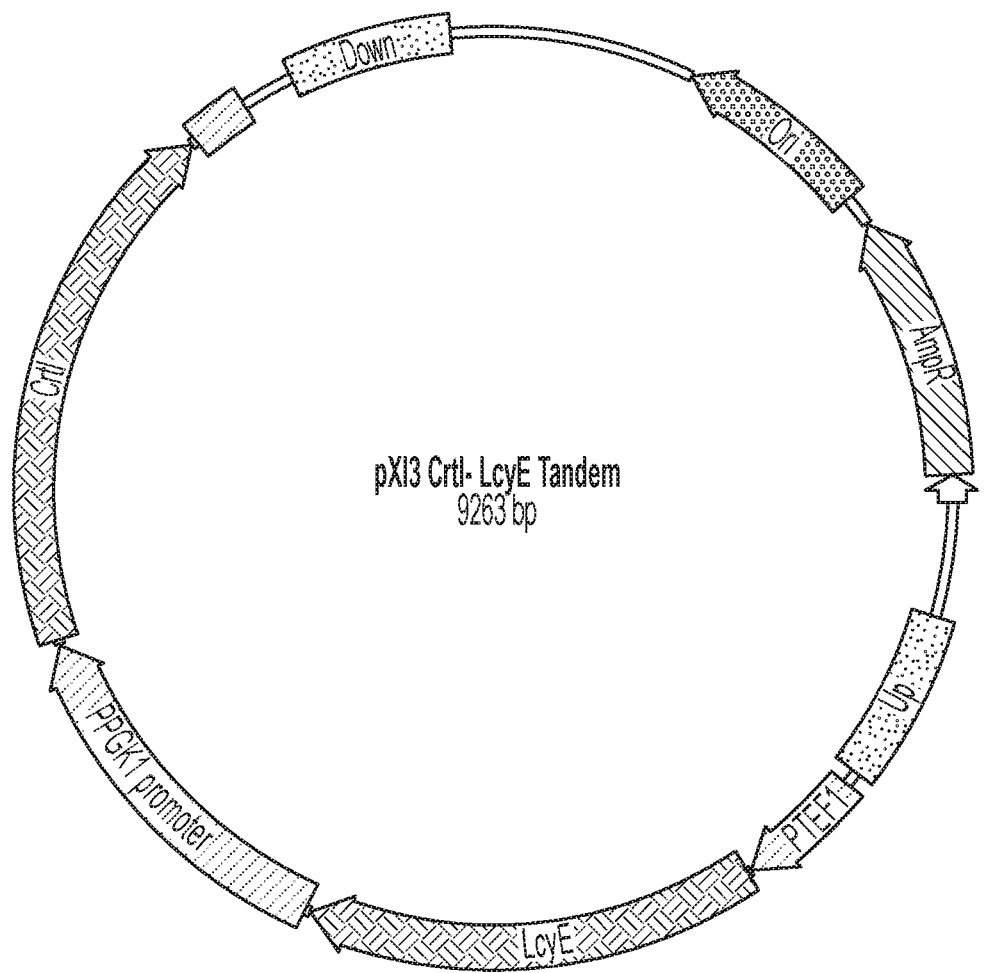
FIG. 16 is a plasmid map of an XI-3 tandem vector containing the crtI and lycE genes.
Figure 17:
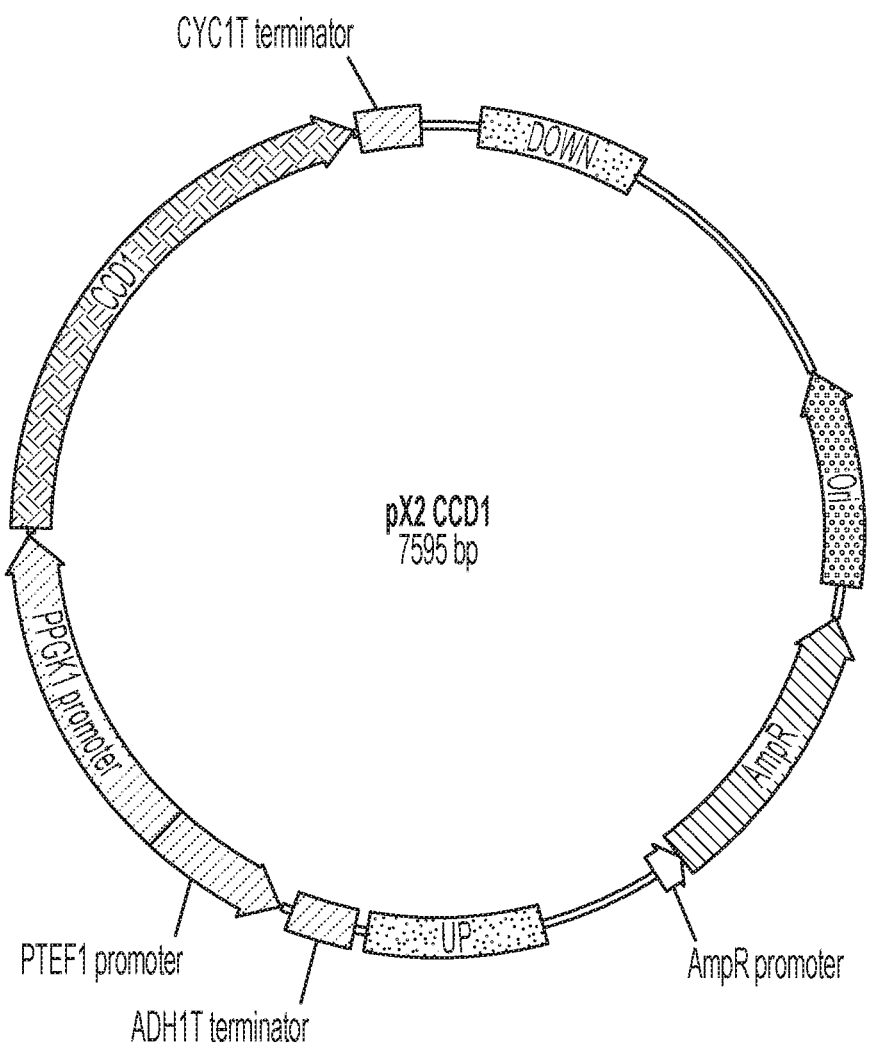
FIG. 17 is a plasmid map of an X-2 vector containing the ccd1 gene.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved method for producing α-ionone.

Alpha-ionone belongs to the $C_{13}$-apocarotenoid or $C_{13}$-norisoprenoid class of compounds. Apocarotenoids are natural aromatic compounds produced in green land plants by the enzymatic cleavage of carotenoids. Carotenes are forty-carbon molecules ($C_{40}$) whose biosynthesis depends on the availability of two $C_5$ universal isoprene-building units: isopentenyl pyrophosphate (IPP) and dimethylallyl pyrophosphate (DMAPP). Isoprene biosynthesis can be carried out through the mevalonate pathway (MVA) or, alternatively, by the 1-deoxy-D-xylulose-5-phosphate (DXP) pathway. Because MVA pathway is naturally present in *S. cerevisiae*, the present invention uses this organism for carotene biosynthesis. The last native step involved in the natural apocarotenoid pathway depends on an endogenous farnesyl pyrophosphate synthase (FPPs). From there, heterologous geranylgeranyl pyrophosphate synthase (crtE), phytoene synthase (crtB), phytoene desaturase (crtI), lycopene ε-cyclase (LycE) and a Carotenoid Cleavage Dioxygenase (CCD1) are required to complete the synthesis of α-ionone.

Lycopene ε-cyclase can produce either monocyclic δ-carotene or dicyclic ε-carotene. Most green land plants such as *Arabidopsis thaliana* or *Solanum lycopersicum* have lycopene ε-cyclases with preferential monocyclic activity that yields δ-carotene as the main product. However, lycopene ε-cyclase from lettuce (*Lactuca sativa*) performs an effective double cyclization of lycopene to produce primarily ε-carotene. Using modified proteins and site-specific mutations (single amino acid mutation of leucine to histidine) gives *A. thaliana* LycE double cyclization activity similar to lycopene ε-cyclases from *L. sativa* (see reference 4) in *E. coli* cells. The impact of this single amino acid change was also validated in an L461H LycE mutant from *Zea mays* in *E. coli* cells. Although both δ- and ε-carotenes could be substrates for CCD1 cleavage for α-ionone production, ε-carotene provides better yields because the stoichiometry produces two molecules of α-ionone per molecule of ε-carotene.

Genes that encode carotenogenic and carotenoid cleavage enzymes are described below with sequences shown in FIGS. 3-12. Some of these sequences have been codon optimized for its expression in *S. cerevisiae*. The screening of five different lycopene ε-cyclase candidates has made it possible to find the most effective sequence for the yeast platform.

Lycopene ε-cyclase can produce either monocyclic δ-carotene or dicyclic ε-carotene. Most green land plants such as *Arabidopsis thaliana* or *Solanum lycopersicum* have lycopene.

Geranylgeranyl pyrophosphate synthase from *Xanthophyllomyces dendrorhous* (Xd-crtE); phytoene synthase from *Pantoea agglomerans* (Pa-crtB) or the mutant bifunctional phytoene synthase/lycopene cyclase from *Xanthophyllomyces dendrorhous* (Xd-crtYB*) are described by reference 10 as producing a tetraterpene ($C_{40}$) overproducing *Saccharomyces cerevisiae* that accumulated up to 1.61 g/L of lycopene in a fed-batch glucose fermentation.

Phytoene desaturase from *Blakeslea trispora* (Bt-crtI) or Phytoene desaturase from *Xanthophyllomyces dendrorhous* were used by Chen et al., 2016 (reference 2) for host and pathway engineering in *Saccharomyces cerevisiae* to overproduce lycopene, thereby obtaining up to 1.64 g/L of this tetraterpene. Pathway engineering included enzyme screening of different phytoene desaturases (crtI). Chen et al., 2016 showed that regardless of the combination of crtB and crtE genes, *Blakeslea trispora* crtI increased lycopene production with respect to homologues from other organisms.

Lycopene ε-cyclase from *Lactuca sativa* (Ls-LycE): The only reported native ε-cyclase that has preferred lycopene bi-cyclase over mono-cyclase activity, confirmed by expression in lycopene-producing strain of *Escherichia coli* (see reference 4).

Native and L461H mutated lycopene ε-cyclase from *Zea mays* (Zm-LycE): Bai et al., 2009 (reference 1) isolated and expressed in *E. coli* a maize lycopene ε-cyclase that produced preferentially δ-carotene. Bai et al., 2009 showed that a directed gene mutagenesis of single amino acid (L461H) was sufficient to allow this enzyme to produce mainly ε-carotene.

Lycopene ε-cyclase from the green alga *Chlorella zofingiensis* (Cz-LycE): coding for an enzyme with proven monocyclase activity to yield δ-carotene when it is expressed in lycopene-accumulating strain of *E. coli* (reference 3). This gene has approximately 40% of sequence identity with LycE from green land plants (GLP) and represents a phylogenetic alternative to *Z. mays* or *L. sativa* cyclase genes.

Lycopene ε-cyclase from liverwort *Marchantia polymorpha* (Mp-LycE): liverworts are known to be early land plants, phylogenetically are between green algae and higher GLP. Expression of LycE from *M. polymorpha* produces similar amounts of δ-carotene and ε-carotene.

Carotenoid cleavage dioxygenase from *Petunia hybrida* (Ph-CCD1): to obtain final α-ionone strain(s) it is necessary to express a CCD1 gene to cleave δ and/or ε-carotene. CCD1 enzymes cleavage substrates include either β- or ε-ring carotenoids (see reference 6).

Vectors and cloning. To reconstruct the α-ionone pathway in *S. cerevisiae* it is necessary to clone the carotenogenic genes into suitable expression vectors. The most commonly used plasmids in yeast are integrative and episomal vectors. Although an increase in the number of gene copies can be seen by using episomal vectors, gene integration is preferable due to the resulting higher strain stability over time. In order to perform vector integration, some sequence modules are required for the DNA recombination, strain selection, marker recycling and gene expression. The present invention uses a collection of vectors disclosed in reference 7 without including the marker genes. These plasmids allow integration and expression in a divergent mode of two or more genes per each vector due to the presence of a bidirectional fused promoter, or in a tandem mode, separating the genes by different promoters. Two or more different transcription terminator sequences are placed downstream of each gene, thereby preventing unwanted recombination events. These cloning vectors also contain *E. coli* replication origin and ampicillin resistance sites in order to enable easy amplification of these vectors to obtain sufficient amounts of DNA to transform yeast. Depending on their homologous regions (UP and DOWN), vectors can be integrated in several specific sites of chromosomes X, XI and XII of *S. cerevisiae* by means of a double crossover mechanism. These sites were selected based on their stability, expression levels and growth impact on yeast. FIGS. 13-17 show the minimum set of integrating plasmids needed to construct α-ionone-producing strains of *S. cerevisiae*.

These vectors can be constructed by using different molecular biology techniques: including restriction cloning or PCR-based seamless cloning such as Gibson Assembly or Golden Gate Assembly.

Transformation and selection of strains. Transformation of yeast with integrative vectors can be performed according to general protocols for LiAc/SS carrier DNA/PEG method (see reference 5). Preferably, plasmids are digested with SwaI/SmiI enzyme to linearize the DNA and increase transformation efficiency.

Selection of transformants was performed by plate-color screening and colony PCR. Even though genomic recombination of integrative vectors is much less probable than the simple incorporation event of episomal vector, using 1-5 μg of plasmid per transformation is sufficient to obtain several colonies. Depending on parental strain, carotenogenic transformants could show some phenotypic variability. This is noticeable in the diversity of colony colors obtained in one round of transformation. Visual screening can be useful to isolate different phenotypes for characterization. Usually differences in color between two colonies imply variations in carotenoid levels and/or carotenoid composition. PCR and genomic sequencing can then be used to check that those vectors are correctly integrated on the specific genomic sites.

Strain characterization: carotenoid and $C_{13}$-apocarotenoid analysis. Characterization of the generated strains is required for selecting candidates with the best productive potential. Shake flask cultures containing YPD (yeast extract 10 g/L, peptone 20 g/L, dextrose 20 g/L) medium were used and carotenoids and aroma profiles were studied for each new strain. Carotenoids were extracted in hexane from 48-hour flask cultures. The resulting organic phase was directly analyzed by reverse phase HPLC. Carotenoids quantification in strains allows identification of possible bottlenecks in the pathway. For $C_{13}$-apocarotenoid quantification, including α-ionone, supernatants obtained from 72-hour cultures were extracted with 10% (v/v) dodecane and analyzed by GC-MS.

Example: Construction and characterization of α-ionone-producing strains. Codon optimized gene synthesis was contracted to Genscript and received as pUC57 vectors. Genes and backbone of the expression vectors were amplified through the Phusion polymerase enzyme (NEB), using primers that contain homologous sequences for Gibson Assembly. PCR products were separated by electrophoresis and extracted by using a Promega purification kit. Purified PCR products were mixed with Gibson Assembly mix (New England Biolabs) and incubated for two hours at 50° C. Gibson reaction products were transformed in competent cells (*E. coli* TOP10, Thermo Scientific) and plated in LBA (LB medium with ampicillin). Screening of transformants was done by colony PCR and positive colonies were grown in LBA to purify plasmids by using miniprep kits (Promega). Correct assembly of vectors was checked by sequencing (Macrogen).

Assembled vectors were digested with SwaI/SmiI (Thermo Scientific) for three hours at 37° C. and 2 μg of digestion products were used directly for *S. cerevisiae* transformation. Yeast transformation was performed as described in the LiAc/SS carrier DNA/PEG method (for example see reference 5), and plated on YPD medium. After 10-15 transformant colonies were re-plated, PCR was used to confirm whether vectors were correctly inserted at specific genomic sites. Genomic DNAs were isolated with a purification kit (Promega) and final strains were confirmed by sequencing (Macrogen). As mentioned above, to construct α-ionone producing strains it is necessary to transform with a minimum of five genes that can be grouped preferably in two vectors and co-transformed simultaneously.

For quantitative carotenoid profiling, 2-5 mL of each culture was centrifuged, and pellets were washed with water. The pelleted cells were disrupted in 1 mL of hexane using 500 μL of glass beads to extract the carotenoids. Extracts were analyzed by reverse phase HPLC. Chromatography was carried on a $C_{18}$ column, at 0.5 mL/min and 45° C., using a mobile phase composed of 85% acetonitrile, 10% methanol and 5% isopropanol. Lycopene, δ-carotene, ε-carotene, and β-carotene were then quantified (see FIG. 19).

For GC-MS identification and quantification of α-ionone, a 20 μL sample of the organic phase was pipetted into a 20 mL headspace vial and diluted with 5 mL of a 30% (w/v) aqueous sodium chloride solution. For quantification, 50 μL of a 1-ppm ethanolic solution of β-damascenone-d4 was added to the vial. Automated headspace solid-phase microextraction HS-SPME was performed with a TriPlusRSH sampler robot.

Separation, identification and quantification of $C_{13}$-apocarotenoids (β-ionone, α-ionone, geranyl-acetone, pseudo-ionone) were carried out by gas chromatography-mass spectrometry (SHIMADZU GCMS-QP2010) using a DB-WAXetr column (0.25 μm, 30 m×0.25 ID).

Table 1 (below) shows the α-ionone concentrations detected in dodecane extracts of 72-hr. cultures in mg/L of dodecane extracted and the mg of α-ionone per mg of cell dry weight. Note that strain αε-1 is more productive than strain αε-3.

TABLE 1

Characterization of alpha-ionone producing strains of *Saccharomyces cerevisiae* (CEN.PK based).

| Strain | Genotype | OD600 | alpha-ionone in dodecane layer (mg/L) | alpha-ionone (mg/g) |
|---|---|---|---|---|
| αε-1 | Xd-crtYB*, Xd-crtE, Xd-crtI, Ls-LycE. Ph-CCD1 | 20 | 90 | 1.07 |
| αε-3 | Xd-crtYB*, Xd-crtE, Xd-crtI, Ls-LycE, Ph-CCD1, Zm-LcyE | 15 | 52 | 0.86 |

Figure 18:
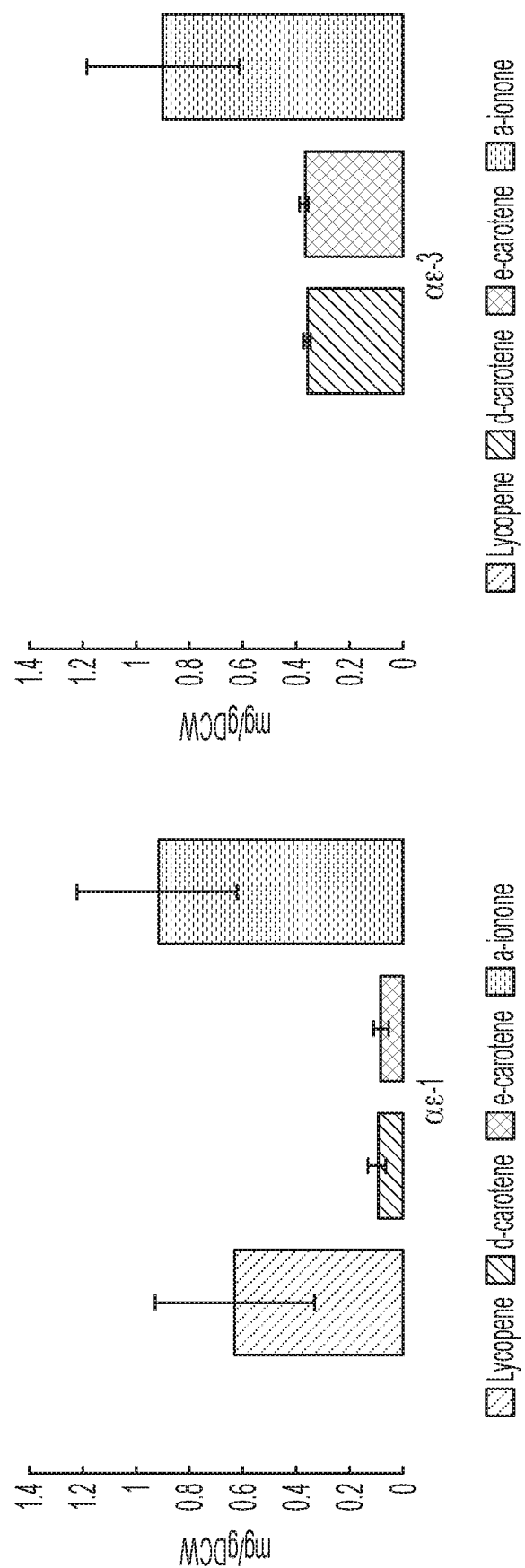
FIG. 18 shows the specific α-ionone yield in mg/g of dry cell weight (DCW), as well as the residual carotenoidsm, of the characterized strains.
Figure 19:
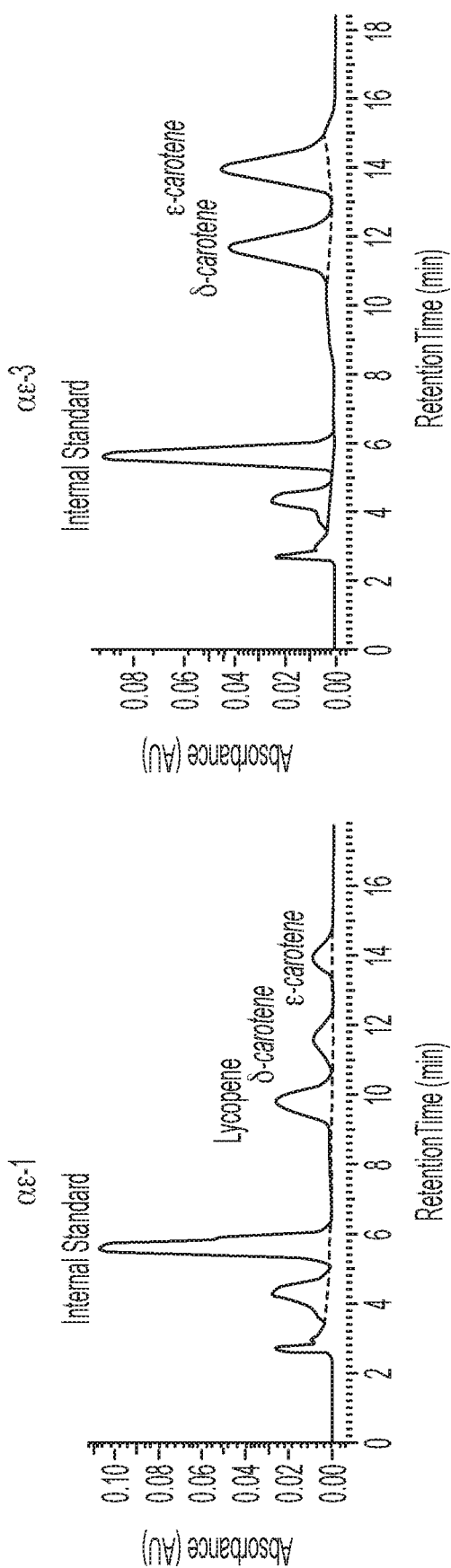
FIG. 19 shows the carotenoid profiles of αε-1 and αε-3 strains.

FIG. 18 summarizes the α-ionone yield in mg/g dry cell weight (DCW) and residual carotenoids after 72 hours cultivation in shake flasks. Table 1 indicates that αε-1 strain is a more suitable construct for production of α-ionone because it has greater ionone content, specific target production and room for improvements (δ-carotene and ε-carotene content is shown in FIG. 19).

Lycopene is the main carotenoid present in the cells and its accumulation appears to be detrimental for yeast growth. An increased efficiency of the LcyE (cyclase) and CDD1 activities are crucial for both detoxification and higher α-ionone production.

The following claims are thus to be understood to include what is specifically illustrated and described above, and what can be obviously substituted. Those skilled in the art will appreciate that various adaptations and modifications of the just-described preferred embodiment can be configured without departing from the scope of the invention. The illustrated embodiment has been set forth only for the purposes of example and should not be taken as limiting the invention.

REFERENCES

[1] Bai, L., Kim, E. H., Dellapenna, D., Brutnell, T. P. (2009) Novel lycopene epsilon cyclase activities in maize revealed through perturbation of carotenoid biosynthesis. Plant J 59:588-599.
[2] Chen, Y., Xiao, W., Wang, Y., Liu, H., Li, X., Yuan, Y. (2016) Lycopene overproduction in *Saccharomyces cerevisiae* through combining pathway engineering with host engineering. Microb Cell Fact 15:113.
[3] Cordero, B. F., Couso, I., Leon, R., Rodriguez, H., Vargas, M. A. (2012) Isolation and characterization of a lycopene ε-Cyclase gene of *Chlorella* (*Chromochloris*) *zofingiensis*. Regulation of the carotenogenic pathway by nitrogen and light. Mar Drugs 10:2069-2088.
[4] Cunningham, F. X., Gantt, E. (2001) One ring or two? Determination of ring number in carotenoids by lycopene ε-cyclases. Proc Natl Acad Sci USA 98:2905-2910.
[5] Gietz, R. D. (2014) Yeast transformation by the LiAc/SS carrier DNA/PEG method. In: Yeast Protocols, 3rd edn. Humana Press, New York.
[6] Huang, F. C., Horvath, G., Molnar, P., Turcsi, E., Deli, J., Schrader, J., Sandmann, G., Schmidt, H., Schwab, W. (2009) Substrate promiscuity of RdCCD1, a carotenoid cleavage oxygenase from *Rosa damascena*. Phytochemistry 70:457-464.
[7] Mikkelsen, M D, Buron, L D, Salomonsen, B., Olsen, C. E., Hansen, B. G., Mortensen, U. H., Halkier, B. A. (2012) Microbial production of indolylglucosinolate through engineering of a multi-gene pathway in a versatile yeast expression platform. Metab Eng 14:104-111.
[8] Werkhoff, P., Bretschneider, W., Güntert, M., Hopp, R., Surburg, H. (1991) Chirospecific analysis in flavor and essential oil chemistry part B. Direct enantiomer resolution of trans-α-ionone and trans-α-damascone by inclusion gas chromatography. Eur Food Res Technol 192:111-115.
[9] Wang, C., Liwei, M., Park, J. B., Jeong, S. H., Wei, G., Wang, Y., Kim, S. W. (2018) Microbial Platform for Terpenoid Production: *Escherichia coli* and Yeast. Front. Microbiol. 9:2460
[10] Xie, W., Lv, X., Ye, L., Zhou, P., Yu, H. (2015) Construction of lycopene-overproducing *Saccharomyces cerevisiae* by combining directed evolution and metabolic engineering. Metab Eng 30:69-78.

What is claimed is:

1. A method of producing enantiomerically pure (R)-(E)-(+)-alpha-ionone in a yeast comprising the steps of:
    (a) constructing recombinant yeast cells that overexpress native nucleic acids, or modified versions thereof, encoding at least one enzyme of the mevalonate pathway for synthesizing farnesyl pyrophosphate, wherein expression of the one or more enzymes is under control of constitutive or inducible promoters;
    (b) modifying the recombinant yeast cells from step (a) to further comprise heterologous nucleic acids that encode enzymes of an apocarotenoid pathway for synthesizing alpha-ionone, wherein said apocarotenoid pathway includes (i) geranylgeranyl pyrophosphate synthase that condenses farnesyl pyrophosphate and isopentenyl pyrophosphate to form geranylgeranyl pyrophosphate, (ii) bifunctional phytoene synthase/lycopene cyclase from *Xanthophyllomyces dendrorhous* that condenses two molecules of geranylgeranyl pyrophosphate to form phytoene, (iii) phytoene desaturase from *Blakeslea trispora* or phytoene desaturase from *Xanthophyllomyces dendrorhous* that converts phytoene to lycopene, (iv) lycopene ε-cyclase from *Latuca sativa* that cyclizes lycopene to form δ-carotene and/or ε-carotene, and (v) CCD1 that cleaves δ-carotene and/or ε-carotene to produce alpha-ionone.

2. The method of claim 1, wherein the yeast cells are selected from the group consisting of *Pichia pastoris, Yarrowia lipolytica*, and *Saccharomyces cerevisiae*.

3. The method of claim 1, wherein the geranylgeranyl pyrophosphate synthase is from *Xanthophyllomyces dendrorhous*.

4. The method of claim 1 further comprising a lycopene ε-cyclase from one or more of the following: *Zea mays, Chromochloris zofingiensis*, and *Marchantia polymorpha*.

5. The method of claim 1, wherein the CCD1 is from *Petunia hybrida, Osmanthus fragrans, Arabidopsis thaliana*, or *Vitis vinifera*.

6. The method of claim 1, wherein the nucleic acids are expressed using yeast centromeric plasmids, high copy number plasmids or integration plasmids, and integrated into specific and stable yeast genomic sites.

7. The method of claim 1, wherein the alpha-ionone is produced in an amount greater than 1 mg per gram of dry cell weight.

8. The method of claim 7, wherein the alpha-ionone is produced in less than 100 hours.

9. The method of claim 1, wherein the recombinant yeast cells are transformed to include nucleic acids that code for peptides having the sequences of SEQ ID NO: 1, SEQ ID NO: 3, SEQ ID NO: 4, SEQ ID NO: 7 and SEQ ID NO: 10.

\* \* \* \* \*